US010918372B2

(12) United States Patent
Brunsvold et al.

(10) Patent No.: US 10,918,372 B2
(45) Date of Patent: Feb. 16, 2021

(54) SUTURE ANCHOR

(71) Applicant: Parcus Medical LLC, Sarasota, FL (US)

(72) Inventors: Mark D. Brunsvold, Sarasota, FL (US); Bart Bracy, Orlando, FL (US)

(73) Assignee: Parcus Medical LLC, Sarasota, FL (US)

(*) Notice: Subject to any disclaimer, the term of this patent is extended or adjusted under 35 U.S.C. 154(b) by 327 days.

(21) Appl. No.: 14/855,074

(22) Filed: Sep. 15, 2015

(65) Prior Publication Data

US 2016/0066900 A1    Mar. 10, 2016

Related U.S. Application Data

(63) Continuation-in-part of application No. PCT/US2014/030691, filed on Mar. 17, 2014, and a
(Continued)

(51) Int. Cl.
*A61B 17/04* (2006.01)
*A61B 17/86* (2006.01)

(52) U.S. Cl.
CPC ...... *A61B 17/0401* (2013.01); *A61B 17/8645* (2013.01); *A61B 17/8685* (2013.01);
(Continued)

(58) Field of Classification Search
CPC .... A61B 2017/0414; A61B 2017/0441; A61B 17/0401; A61F 2002/0823;
(Continued)

(56) References Cited

U.S. PATENT DOCUMENTS 5,217,486 A    6/1993  Rice et al.
5,269,809 A *  12/1993 Hayhurst ........... A61B 17/0401
                                                    606/151
(Continued)

FOREIGN PATENT DOCUMENTS

DE    10 2011 106653 A1    1/2013
WO         WO97/30649 A1    8/1997
(Continued)

OTHER PUBLICATIONS

File History for U.S. Appl. No. 12/290,226.
(Continued)

*Primary Examiner* — Shaun L David
*Assistant Examiner* — Christina C Lauer
(74) *Attorney, Agent, or Firm* — Michael Bergman; Bergman LLC

(57) ABSTRACT

An anchor device and system for coupling soft tissue to osseous tissue includes a stopper member that supports a loop of suture material. A fixing member includes features that allow it to be rigidly coupled to surrounding bone and thus hold the stopper member in a cavity within the bone. The loop of suture material, in turn, supports a second suture device, which is coupled to, and thus retains, the soft tissue. In certain embodiments, the fixing member includes a wadding structure having a generally elastic property.

14 Claims, 45 Drawing Sheets

Related U.S. Application Data continuation-in-part of application No. 12/290,226, filed on Oct. 27, 2008, now Pat. No. 9,277,909, said application No. PCT/US2014/030691 is a continuation-in-part of application No. 12/290,226, filed on Oct. 27, 2008, now Pat. No. 9,277,909.

(60) Provisional application No. 61/787,373, filed on Mar. 15, 2013, provisional application No. 61/127,315, filed on May 12, 2008, provisional application No. 60/983,159, filed on Oct. 27, 2007.

(52) U.S. Cl.
CPC . *A61B 2017/0403* (2013.01); *A61B 2017/044* (2013.01); *A61B 2017/0406* (2013.01); *A61B 2017/0412* (2013.01); *A61B 2017/0414* (2013.01); *A61B 2017/0432* (2013.01); *A61B 2017/0445* (2013.01); *A61B 2017/0458* (2013.01); *A61B 2017/0475* (2013.01)

(58) Field of Classification Search
CPC ...... A61F 2002/0888; A61F 2002/0835; A61F 2002/0817; A61F 2/08
See application file for complete search history.

(56) References Cited

U.S. PATENT DOCUMENTS

| | | | |
|---|---|---|---|
| 5,480,403 | A | 1/1996 | Lee et al. |
| 5,569,306 | A | 10/1996 | Thal |
| 5,593,410 | A | 1/1997 | Vrespa |
| 5,658,313 | A | 8/1997 | Thal |
| 5,665,112 | A | 9/1997 | Thal |
| 5,683,419 | A | 11/1997 | Thal |
| 5,899,921 | A | 5/1999 | Caspari et al. |
| 5,902,321 | A | 5/1999 | Caspari et al. |
| 5,906,632 | A | 5/1999 | Bolton |
| 5,935,129 | A | 8/1999 | McDevitt et al. |
| 5,957,953 | A | 9/1999 | DiPoto et al. |
| 5,964,768 | A | 10/1999 | Huebner |
| 6,027,523 | A | 2/2000 | Schmieding |
| 6,508,830 | B2 | 1/2003 | Steiner |
| 6,527,794 | B1 | 3/2003 | McDevitt et al. |
| 6,575,976 | B2 | 6/2003 | Grafton |
| 6,585,730 | B1 | 7/2003 | Foerster |
| 6,641,596 | B1 | 11/2003 | Lizardi |
| 6,652,563 | B2 | 11/2003 | Dreyfuss |
| 6,692,516 | B2 | 2/2004 | West, Jr. et al. |
| 6,840,953 | B2 | 1/2005 | Martinek |
| 6,855,157 | B2 | 2/2005 | Foerster et al. |
| 6,923,824 | B2 | 8/2005 | Morgan et al. |
| 6,984,241 | B2 | 1/2006 | Lubbers et al. |
| 7,081,126 | B2 | 7/2006 | McDevitt et al. |
| 7,226,469 | B2 | 6/2007 | Benavitz et al. |
| 7,381,213 | B2 | 6/2008 | Lizardi |
| 2001/0021862 | A1 | 9/2001 | Bonutti et al. |
| 2001/0025181 | A1* | 9/2001 | Freedlan ............ A61B 17/0401 606/54 |
| 2002/0052629 | A1 | 5/2002 | Morgan et al. |
| 2002/0052630 | A1 | 5/2002 | Morgan et al. |
| 2002/0077631 | A1 | 6/2002 | Lubbers et al. |
| 2002/0095180 | A1 | 7/2002 | West, Jr. et al. |
| 2003/0060887 | A1 | 3/2003 | Ek |
| 2003/0130695 | A1 | 7/2003 | McDevitt et al. |
| 2003/0149448 | A1 | 8/2003 | Foerster et al. |
| 2003/0195563 | A1 | 10/2003 | Foerster |
| 2003/0225456 | A1 | 12/2003 | Ek |
| 2004/0002735 | A1 | 1/2004 | Lizardi et al. |
| 2004/0093031 | A1 | 5/2004 | Burkhart et al. |
| 2004/0098052 | A1 | 5/2004 | West, Jr. et al. |
| 2004/0193167 | A1 | 9/2004 | Tucciarone et al. |
| 2005/0033363 | A1 | 2/2005 | Borjarski et al. |
| 2005/0055052 | A1 | 3/2005 | Lombardo et al. |
| 2005/0075668 | A1 | 4/2005 | Lizardi |
| 2005/0149122 | A1 | 7/2005 | McDevitt et al. |
| 2005/0234460 | A1 | 10/2005 | Miller |
| 2005/0240199 | A1 | 10/2005 | Martinek et al. |
| 2005/0240226 | A1 | 10/2005 | Foerster et al. |
| 2005/0245932 | A1 | 11/2005 | Fanton et al. |
| 2005/0267479 | A1 | 12/2005 | Morgan et al. |
| 2006/0079904 | A1 | 4/2006 | Thal |
| 2006/0106423 | A1 | 5/2006 | Weisel et al. |
| 2006/0201519 | A1 | 9/2006 | Frazier et al. |
| 2006/0207606 | A1 | 9/2006 | Roue et al. |
| 2006/0207608 | A1 | 9/2006 | Hirotsuka et al. |
| 2006/0207612 | A1 | 9/2006 | Jackson et al. |
| 2006/0259076 | A1 | 11/2006 | Burkhart et al. |
| 2006/0271060 | A1 | 11/2006 | Gordon |
| 2006/0282081 | A1 | 12/2006 | Fanton et al. |
| 2006/0282083 | A1 | 12/2006 | Fanton et al. |
| 2007/0049944 | A1 | 3/2007 | Stone et al. |
| 2007/0073299 | A1 | 3/2007 | Dreyfuss et al. |
| 2007/0135841 | A1 | 6/2007 | Dreyfuss |
| 2007/0142835 | A1 | 6/2007 | Green et al. |
| 2007/0156148 | A1 | 7/2007 | Fanton et al. |
| 2007/0156149 | A1 | 7/2007 | Fanton et al. |
| 2007/0156150 | A1 | 7/2007 | Fanton et al. |
| 2007/0156176 | A1 | 7/2007 | Fanton et al. |
| 2007/0203498 | A1 | 8/2007 | Gerber et al. |
| 2007/0219557 | A1 | 9/2007 | Bourque et al. |
| 2007/0219558 | A1 | 9/2007 | Deutsch |
| 2007/0225719 | A1 | 9/2007 | Stone et al. |
| 2007/0255317 | A1 | 11/2007 | Fanton et al. |
| 2007/0260259 | A1 | 11/2007 | Fanton et al. |
| 2008/0004659 | A1 | 1/2008 | Burkhart et al. |
| 2008/0009904 | A1 | 1/2008 | Bourque et al. |
| 2008/0015540 | A1 | 1/2008 | Muni et al. |
| 2008/0023012 | A1 | 1/2008 | Dineen et al. |
| 2008/0027560 | A1 | 1/2008 | Jackson et al. |
| 2008/0033460 | A1 | 2/2008 | Ziniti et al. |
| 2008/0035160 | A1 | 2/2008 | Woodson et al. |
| 2008/0051836 | A1 | 2/2008 | Foerster et al. |
| 2008/0058584 | A1 | 3/2008 | Hirotsuka et al. |
| 2008/0065114 | A1* | 3/2008 | Stone ................. A61B 17/0401 606/139 |
| 2008/0086138 | A1 | 4/2008 | Stone et al. |
| 2008/0103528 | A1 | 5/2008 | Zirps et al. |
| 2008/0109038 | A1 | 5/2008 | Steiner et al. |
| 2008/0161864 | A1 | 7/2008 | Beck et al. |
| 2008/0208265 | A1 | 8/2008 | Frazier et al. |
| 2008/0215091 | A1 | 9/2008 | Dreyfuss |
| 2008/0249567 | A1 | 10/2008 | Kaplan |
| 2011/0264141 | A1 | 10/2011 | Denham et al. |
| 2012/0150223 | A1 | 6/2012 | Manos et al. |
| 2012/0239085 | A1 | 9/2012 | Schlotterback et al. |

FOREIGN PATENT DOCUMENTS

| | | |
|---|---|---|
| WO | WO-2000/044293 | 8/2000 |
| WO | WO 2006/099109 A2 | 9/2006 |
| WO | WO 2007/109769 A1 | 9/2007 |
| WO | WO-2008/097403 | 8/2008 |

OTHER PUBLICATIONS

File History for U.S. Appl. No. 61/127,315.
File History for U.S. Appl. No. 60/983,159.
File History for U.S. Appl. No. 61/787,373.
File History for U.S. Appl. No. 15/057,077.
File History for U.S. Serial No. PCT/US14/30691.

* cited by examiner

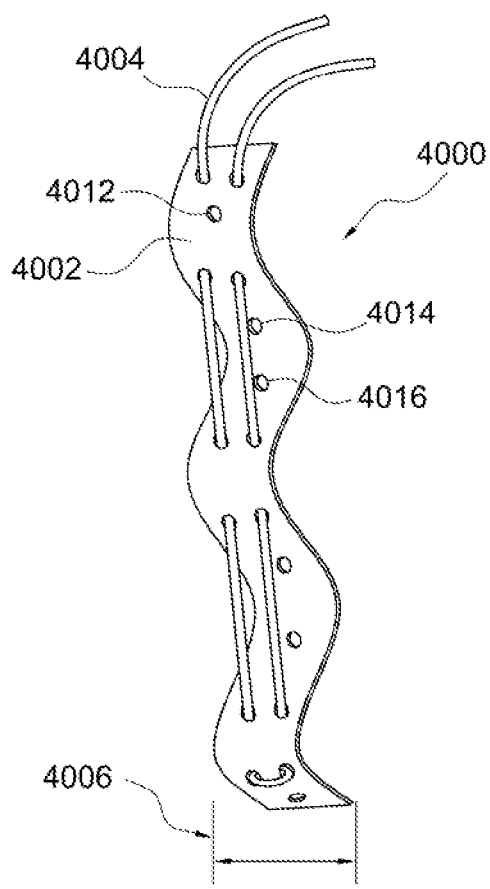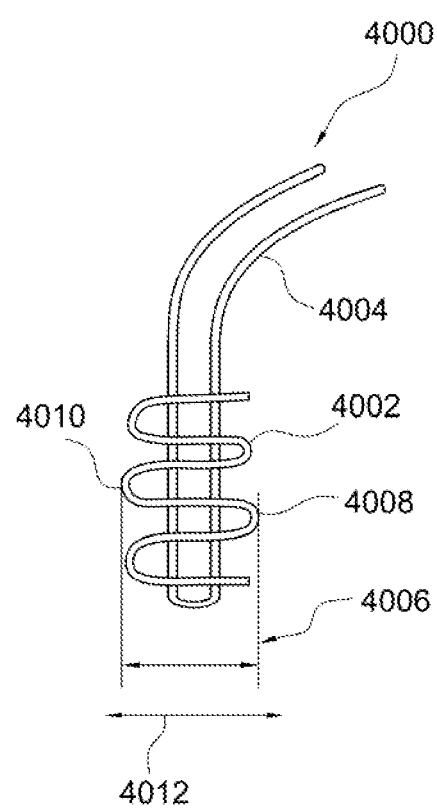
FIG. 40A
FIG. 40B

SUTURE ANCHOR

CROSS-REFERENCE TO RELATED APPLICATIONS

The present application is a continuation-in-part of PCT patent application number PCT/US2014/030691 filed Mar. 17, 2014, which claims the benefit of U.S. provisional patent application No. 61/787,373 filed on Mar. 15, 2013 (and which also is a continuation-in-part of U.S. non-provisional patent application Ser. No. 12/290,226 filed Oct. 27, 2008, and claims, therethrough, the benefit of U.S. provisional patent applications No. 60/983,159 filed on Oct. 27, 2007 and 61/127,315 filed on May 12, 2008). The present application is also a continuation-in-part of U.S. non-provisional patent application Ser. No. 12/290,226, filed Oct. 27, 2008, and claims, therethrough, the benefit of U.S. provisional patent applications No. 60/983,159 filed on Oct. 27, 2007 and 61/127,315 filed on May 12, 2008. The disclosures of all of the foregoing are incorporated by reference in their entireties in the present application.

FIELD OF THE INVENTION

The present invention relates to surgical devices and more particularly to devices for surgical attachment.

BACKGROUND

Various surgical procedures require the temporary or permanent coupling of tissue to hard tissue such as bone. For example, when a tendon or ligament becomes detached from the bone which normally supports it, reattachment of the soft tissue to the bone with a supporting device helps to position the soft tissue for regrowth and recovery. Under other circumstances it is desirable to have a secure means of attaching a length of suture material between one or more bony regions. With this in mind, a variety of approaches have been developed for securing suture to hard tissue such as bone. Classed generally as bone anchors, these approaches have met with varying success.

Certain devices among those in this class have provided limited coupling strength with respect to a surrounding bone substrate matrix. Other devices have provided limited coupling strength and durability with respect to a suture material. Others have provided inadequate positional adjustability of the suture material. These and other deficiencies persist despite long and well-funded efforts by many investigators to secure improved methods and devices.

SUMMARY

Being aware of the long and previously incompletely effective efforts of others to address these problems, the present inventor has arrived at a new and important understanding of the problems, and of the mechanisms underlying those problems. Having developed this knowledge through careful and diligent effort, the inventor has now conceived and, out of similarly diligent efforts, reduced to practice novel and effective solutions to these problems. In particular, it is understood that earlier efforts to anchor soft tissue to bone have been inconsistently effective. The inventor now presents new and effective methods, devices and systems to effect these and other purposes.

As discussed above, it is necessary in some surgical procedures to provide a mechanism for coupling soft tissue to a particular location within the body. For example, in some circumstances it is necessary to couple a ligament or tendon to a bone. In other circumstances soft tissue such as muscle or skin must be similarly fixed in place.

One method of achieving such a coupling is to embed at least a portion of an anchor within a bone, and couple a suture between the anchor and the soft tissue. To this end, the present invention includes methods, systems and apparatus for providing an anchor device including a suture for coupling between, for example, bone and soft tissue.

In one embodiment, the anchor device includes a stopper portion and a fixing portion. The stopper portion is adapted to be coupled to a loop of suture material. A further length of suture material is disposed in a bent configuration through the suture loop. The stopper portion is disposed within a substrate matrix of osseous tissue and held in place by the fixing portion.

In certain embodiments according to the invention, the fixing portion includes a threaded feature on an external surface thereof. In other embodiments according to the invention a fixing portion includes a barbed feature on an external surface thereof. In still other embodiments according to the invention a fixing portion includes a vaned feature on an external surface thereof.

In certain embodiments of the invention, the fixing portion includes a plurality of projecting features disposed between longitudinal grooves at an external surface of the fixing portion. In other embodiments of the invention, the fixing portion includes a plurality of barb projections where the barb projections include substantially circular barb projections disposed coaxially about a longitudinal axis of the fixing portion. In other embodiments, the barb projections include a plurality of projections disposed between longitudinal grooves at a surface of the fixing portion.

In certain embodiments of the invention, the stopper portion is disposed between two or more fixing portions. In certain embodiments of the invention, fixing portions are provided with opposite threads and a coupling mechanism. In still further embodiments of the invention, the stopper portion includes a threaded surface feature oppositely handed with respect to a threaded surface feature of a fixing portion. In certain embodiments, the stopper portion includes a detent mechanism adapted to couple the stopper portion in substantially fixed spatial relationship with respect to the fixing portion.

These and other advantages and features of the invention will be more readily understood in relation to the following detailed description of the invention, which is provided in conjunction with the accompanying drawings.

BRIEF DESCRIPTION OF THE DRAWINGS

FIGS. 40A-40B illustrate still further features of an anchor prepared according to principles of the invention including features related to deployment of the same;

DETAILED DESCRIPTION

Figure 1:
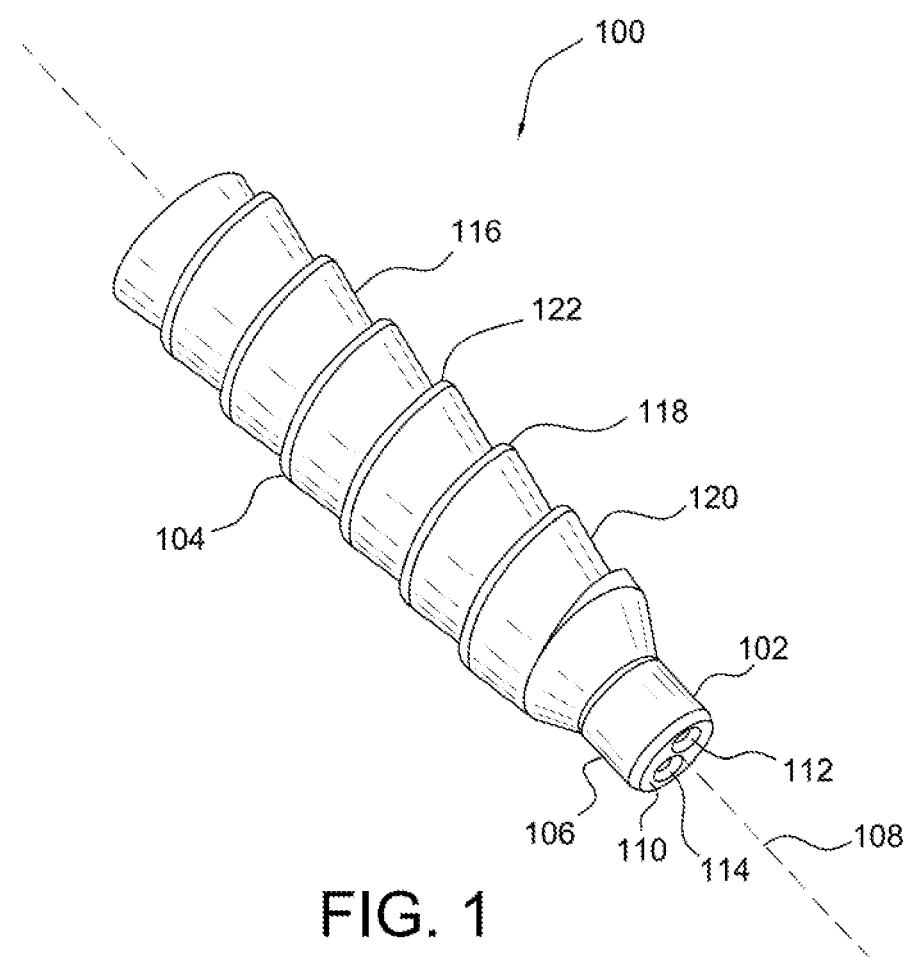
FIG. 1 shows, in perspective side view, an exemplary anchor device including a stopper portion and a fixing portion according to one embodiment of the invention.

FIG. 1 shows part of an exemplary anchor 100 according to one embodiment of the invention. The anchor 100 includes a first stopper portion 102 and a second fixing portion 104. The stopper portion 102 has a substantially circular cylindrical peripheral surface 106 disposed coaxially about a longitudinal axis 108. A distal surface 110 of the stopper 102 is disposed substantially normal to the longitudinal axis 108. In the illustrated embodiment, first and second bores are defined within the stopper 102. Each bore is defined by a respective substantially cylindrical internal surface 112, 114. Internal surfaces 112, 114 have respective longitudinal axes disposed substantially parallel to one another and to longitudinal axis 108.

In the illustrated embodiment, fixing portion 104 of the anchor 102 is generally cylindrical about longitudinal axis 108. A circumferential surface 116 of fixing portion 104 includes a plurality of detent formations. As illustrated, the detent formations include a substantially helical flange 118 or ridge disposed generally equidistant to longitudinal axis 108. As illustrated, the helical flange 118 includes a first distal surface region 120 and a second proximal surface region 122.

As illustrated in FIG. 1, the detent formation is shown as a push-in style detent feature. One of skill in the art will appreciate, however, that other detent features, such as, for example, cortical bone threads and cancellous bone threads are to be used in other respective embodiments of the invention. Also, as shown, the push-in detent features extend over the full length of the fixing portion 104, as shown. In other embodiments partial coverage is employed.

As will be discussed in additional detail below, the fixing portion 104 includes an internal surface defining a bore that is substantially coaxial with longitudinal axis 108. In the configuration illustrated, where the stopper portion 102 is disposed adjacent to a proximal end of the fixing portion 104 open regions within bores 112 and 114 are contiguous with an open region within the longitudinal bore of the fixing portion 104.

According to one embodiment of the invention, the stopper portion 102 is removably coupled to the fixing portion 104 in the illustrated orientation. According to one methodical aspect of the invention stopper portion 102 is removably coupled to fixing portion 104 prior to insertion of the resulting assembly into osseous tissue. In an alternative it embodiment of the invention stopper portion 102 is disposed within a region of osseous tissue and fixing portion 104 is subsequently disposed adjacent to stopper portion 102. In a further embodiment, stopper portion 102 is substantially non-removal.

In one embodiment of the invention, the helical flange 118 is configured as a thread, whereby a method of rotating fixing portion 104 about longitudinal axis 108 causes a threading interaction between helical flange 118 and a surrounding bone tissue. Consequently the rotation of the fixing portion 104 causes a distal advancement of the fixing portion 104 into the bone tissue.

As will be described below further detail, a method according to one embodiment of the invention includes disposing respective first and second portions of a length of suture substantially coaxially within bores 112 and 114. The length of suture includes a further U-shaped portion disposed within the bore of the fixing portion 104 and contiguous with the first and second suture portions. According to one embodiment of the invention, first and second knots are formed at respective ends of the length of suture and are disposed distally of surface 108 so as to slidingly couple the length of suture to the stopper portion 106.

Figure 2:
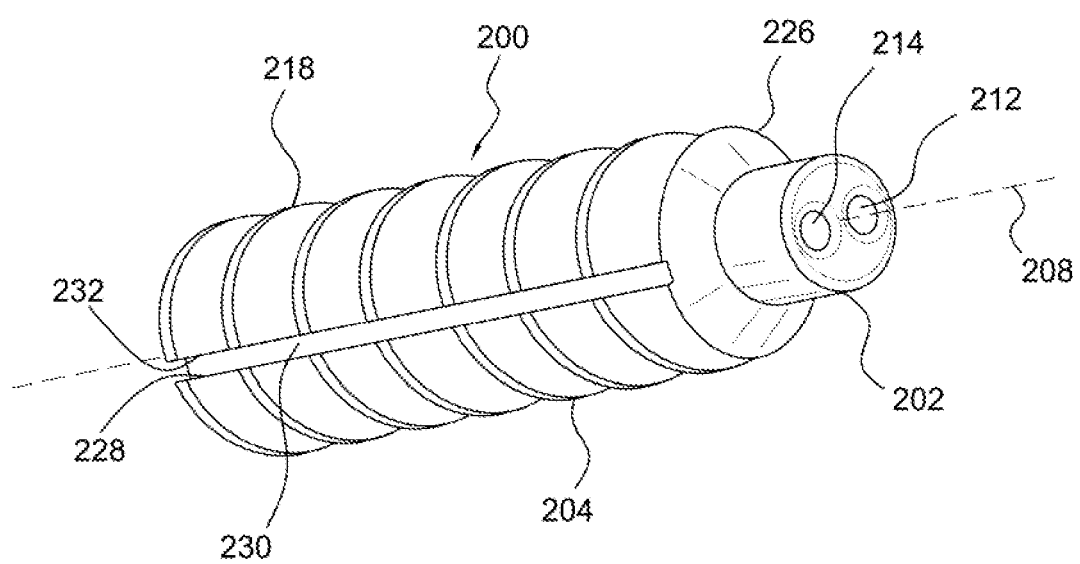
FIG. 2 shows, in perspective side view, an exemplary anchor device including a fixing device having a longitudinal groove according to one embodiment of the invention.

FIG. 2 shows an oblique generally distal perspective view of a portion of an anchor 200 according to one embodiment of the invention. Like anchor 100, anchor 200 includes a stopper portion 202 and a fixing portion 204. The stopper portion 202 includes first and second generally longitudinal bores 212 and 214. In the embodiment shown, the longitudinal bores 212 and 214 are defined by respective substantially cylindrical internal surfaces of the stopper portion 202. According to one embodiment of the invention, these substantially cylindrical internal surfaces are substantially smooth and uninterrupted. The stopper portion 202 is adapted to be disposed adjacent to and in some embodiments coupled to, a distal end 226 of fixing portion 204.

The fixing portion 204 includes a generally cylindrical external surface 216 having a helical flange 218 formation. A groove 228 is disposed longitudinally along surface 216 and defines respective first and second ends of flange 218. In the illustrated embodiment, flange 218 is generally helical. Consequently, flange end 230 is distally offset along a longitudinal axis 208 with respect to flange end 232.

In another embodiment of the invention, the flange 218 formation is substantially circular, rather than helical, so that flange ends 230, 232 are disposed generally adjacent to one another across groove 228. It should be noted that in either case, flange 218 does not form an uninterrupted helical thread about longitudinal axis 218. In a further embodiment, fixing portion 204 includes a plurality of longitudinal grooves disposed generally parallel to groove 228 around longitudinal axis 208.

Figure 3:
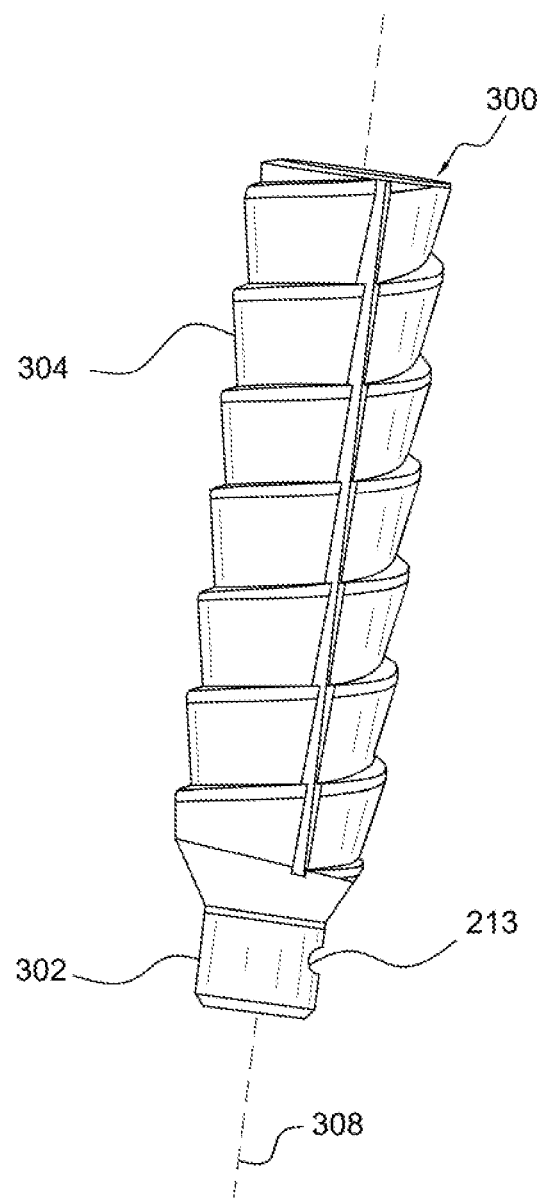
FIG. 3 shows, in perspective side view, an exemplary anchor device including a stopper device having a radial suture loop bore according to one embodiment of the invention.

FIG. 3 shows an anchor 300 including a stopper portion 302 and a fixing portion 304 according to still another embodiment of the invention. While the configuration of anchor 300 is generally similar to that of anchor 200, it should be noted that stopper portion 302 includes a bore 213 disposed generally perpendicular to a longitudinal axis 308.

One of skill in the art will appreciate that bore 213 defines an internal right angle within stopper portion 302 so as to open at a distal end of an internal longitudinal bore within the fixing portion 304. Thus a length of suture can be passed through bore 213 to form an internal loop within the longitudinal bore of the fixing portion. An end of the length of suture projects perpendicular to longitudinal axis to emerge through the illustrated orifice where it is knotted to retain the length of suture in sliding relation to the stopper portion. One of skill in the art will appreciate that this arrangement contrasts to the longitudinal bores 212, 214 of anchor 200.

Figure 4:
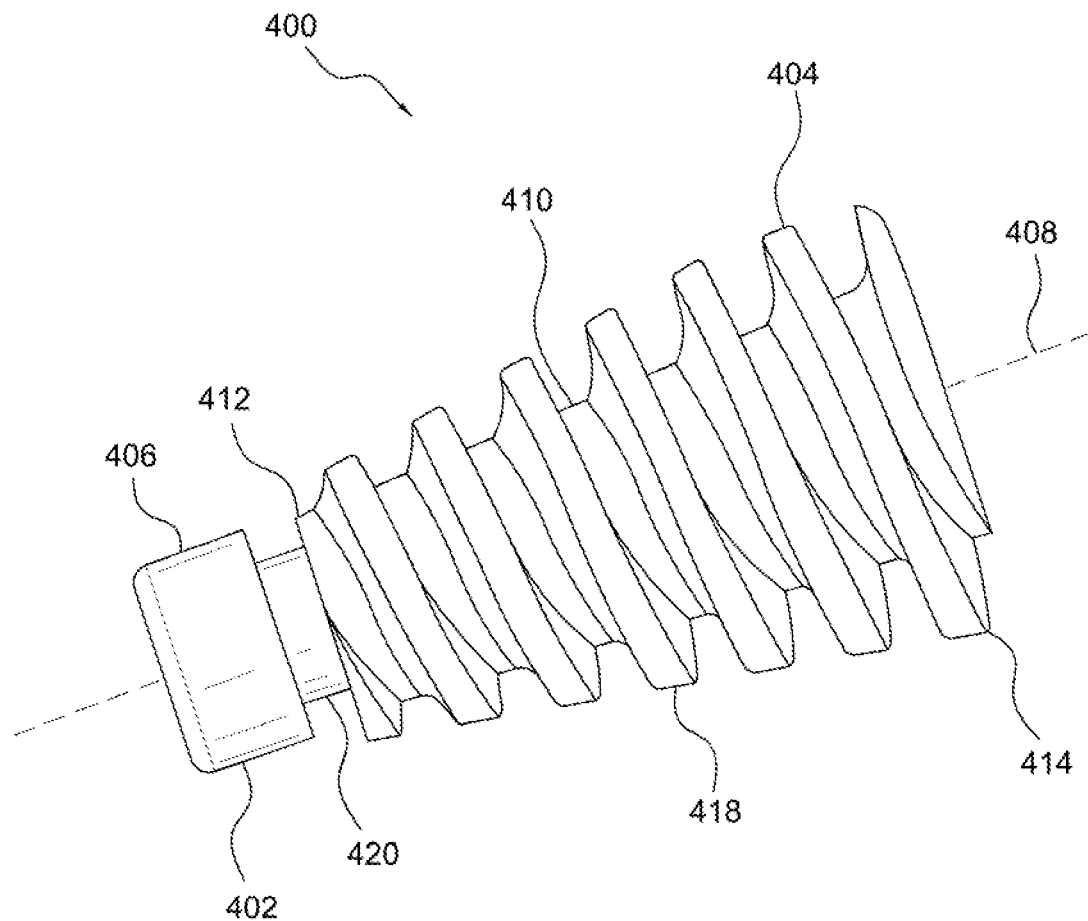
FIG. 4 shows, in perspective side view, an exemplary anchor device including a stopper device having a projection according to one embodiment of the invention.

FIG. 4 shows, in perspective view, a portion of an anchor 400 according to a further embodiment of the invention. The anchor includes a stopper portion 402 and a fixing portion 404. The fixing portion 404 has a generally circular symmetry about a longitudinal axis 408. A circumferential external surface 410 of the fixing portion has a first relatively smaller radius perpendicular to longitudinal axis 408 at a distal end 412 of the fixing portion. In comparison a corresponding radius at a second proximal end 414 of the fixing portion 404 is relatively larger. Consequently, external surface 410 of the fixing portion 404 describes, generally, a frustum of a cone. In the illustrated embodiment, the external surface 410 includes a projecting ridge or flange 418 disposed in a generally spiral/helical configuration about longitudinal axis 408. In various embodiments, the ridge or flange 418 is interrupted by one or more longitudinal grooves like that shown in anchor 300 of FIG. 3. It should be noted that while FIG. 4 exemplifies an anchor having a cortical thread alternative threading and other retaining features are used in alternative embodiments respectively.

In the illustrated embodiment, stopper portion 402 includes a generally circular cylindrical external surface 406 disposed coaxially to axis 408 at a distal region of the stopper. The stopper 402 also has a projecting portion 420 at a proximal region thereof. In various embodiments, as will be described below in additional detail, the projecting portion 420 is adapted to be received within a corresponding cavity of the fixing portion 404. According to one embodiment the corresponding cavity consists of a portion of a longitudinal bore.

Figure 5:
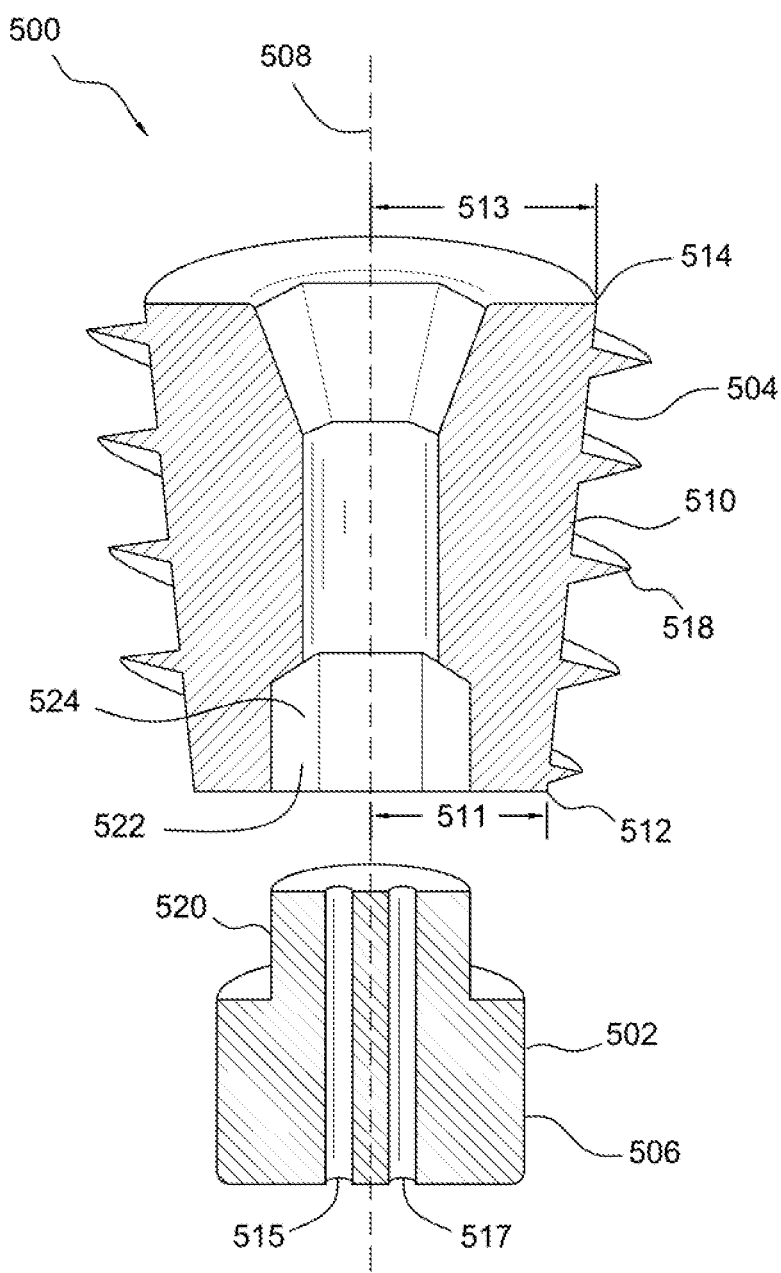
FIG. 5 shows, in cross-section, an anchor according to one embodiment of the invention.
Figure 6A:
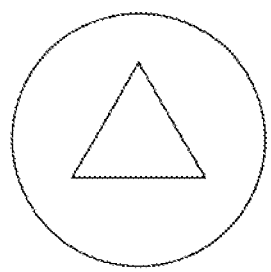
FIGS. 6A-6H show a respective plurality of projection profiles according to respective exemplary embodiments of the invention.
Figure 6B:
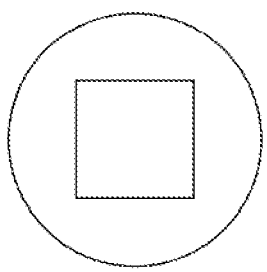
Figure 6C:
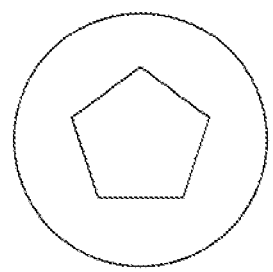
Figure 6D:
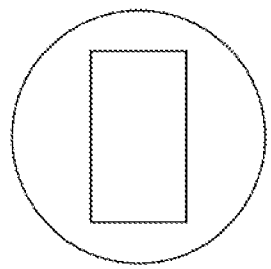
Figure 6E:
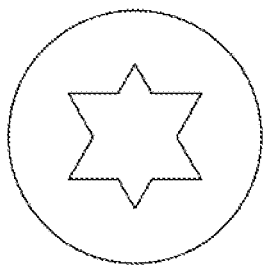
Figure 6F:
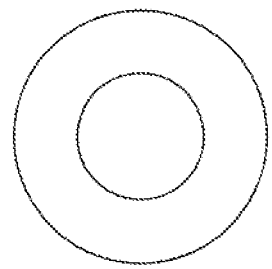
Figure 6G:
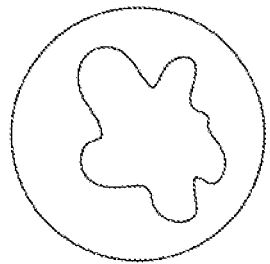
Figure 6H:
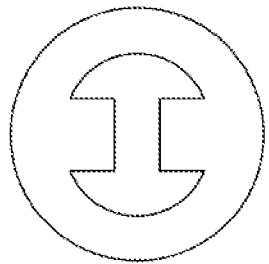

FIG. 5 shows, in cross-section, a portion of an exemplary anchor 500. Anchor 500 includes a stopper portion 502 and a fixing portion 504. The fixing portion 504 has a generally circular symmetry about a longitudinal axis 508. A circumferential external surface 510 of the fixing portion has a first relatively smaller radius 511 perpendicular to longitudinal axis 508 at a distal end 512 of the fixing portion. In comparison a corresponding radius at a second proximal end 514 of the fixing portion 504 is relatively larger. Consequently, external surface 510 of the fixing portion 504 describes, generally, a frustum of a cone.

As shown, longitudinal bores 515, 517 traverse the stopper portion 502. The longitudinal bores are disposed generally parallel to longitudinal axis 508. As will be discussed below in further detail, the longitudinal bores 515, 517 are adapted to receive respective portions of a suture loop.

In the illustrated embodiment, stopper portion 502 includes a generally circular cylindrical external surface 506 disposed coaxial to axis 508 at a distal region of the stopper. The stopper 502 also has a projecting portion 520 at a proximal region thereof. As illustrated, the projecting portion 520 is adapted to be received within a corresponding cavity 522 of the fixing portion 504. As illustrated, cavity 522 is defined by a plurality of substantially planar surface regions, e.g., 524. Consequently, a cross-sectional profile of the cavity 522 is, in certain embodiments, polygonal. A corresponding cross-section of projecting portion 520 matches the polygonal cross-section of the cavity 522, in size and shape, so that the cavity is adapted to receive the projecting portion 520 firmly therewithin.

The creative practitioner of ordinary skill in the art will appreciate that a wide variety of cross-sections are used in corresponding embodiments of the invention. Thus, while the cross-section of projecting portion 520 is shown as generally hexagonal, other useful cross-sections include, as shown in FIG. 6, triangular (FIG. 6A), square (FIG. 6B), pentagonal (FIG. 6C), elongate (FIG. 6D), stellate (FIG. 6E), circular (FIG. 6F), irregular (FIG. 6G) and combinations thereof, (e.g, FIG. 6H).

Figure 7:
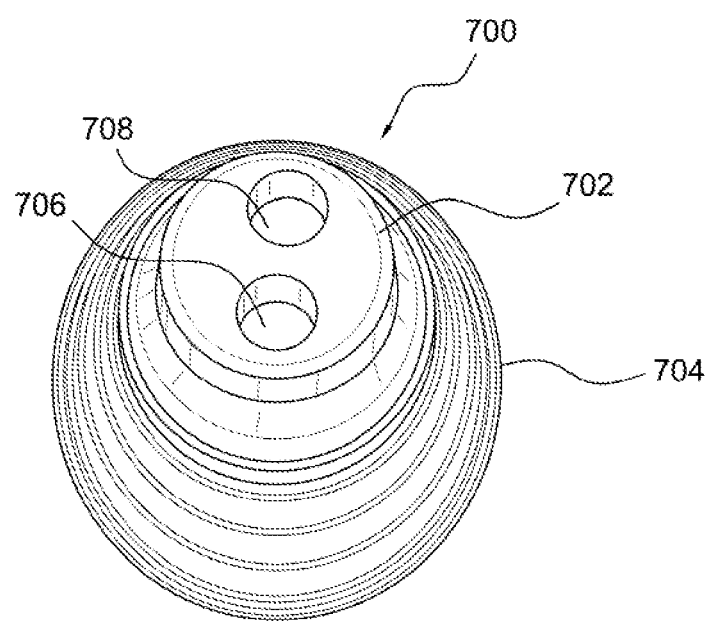
FIG. 7 shows, in distal perspective view, an anchor device according to one embodiment of the invention.

FIG. 7 shows, in distal perspective view, an exemplary anchor 700 including a stopper portion 702 and a fixing portion 704. As is evident on inspection, longitudinal bores 706 and 708 in the stopper portion 702 form a contiguous passage with a longitudinal bore of the fixing portion 704.

Figure 8:
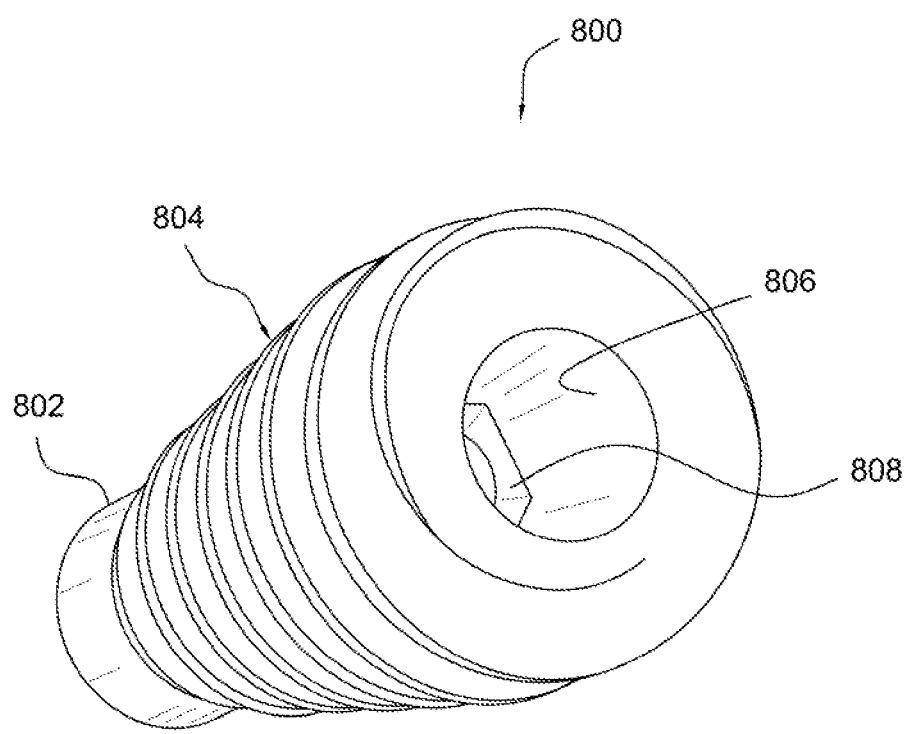
FIG. 8 shows, in proximal perspective view, an anchor device according to one embodiment of the invention.

FIG. 8 shows, in proximal perspective view, an exemplary anchor 800 including a stopper portion 802 and a fixing portion 804. A portion of a longitudinal bore 806 within the fixing portion 804 is visible. As shown, an internal surface of the longitudinal fixing portion 804 includes a plurality of substantially planar surface regions e.g., 808 defining a substantially hexagonal tool engagement region 806.

The substantially hexagonal tool engagement region 806 is adapted to receive a portion of a driving tool of corresponding cross-section therewithin. One of skill in the art will appreciate that such a tool can be used to rotate or otherwise manipulate the fixing portion as part of an anchor insertion procedure and method. It will also be evident to one of skill in the art that, while the illustrated embodiment shows a tool engagement region of the longitudinal bore having a substantially hexagonal cross-section, a wide variety of other cross-sections and configurations can readily be used in various embodiments of the invention.

Figure 9:
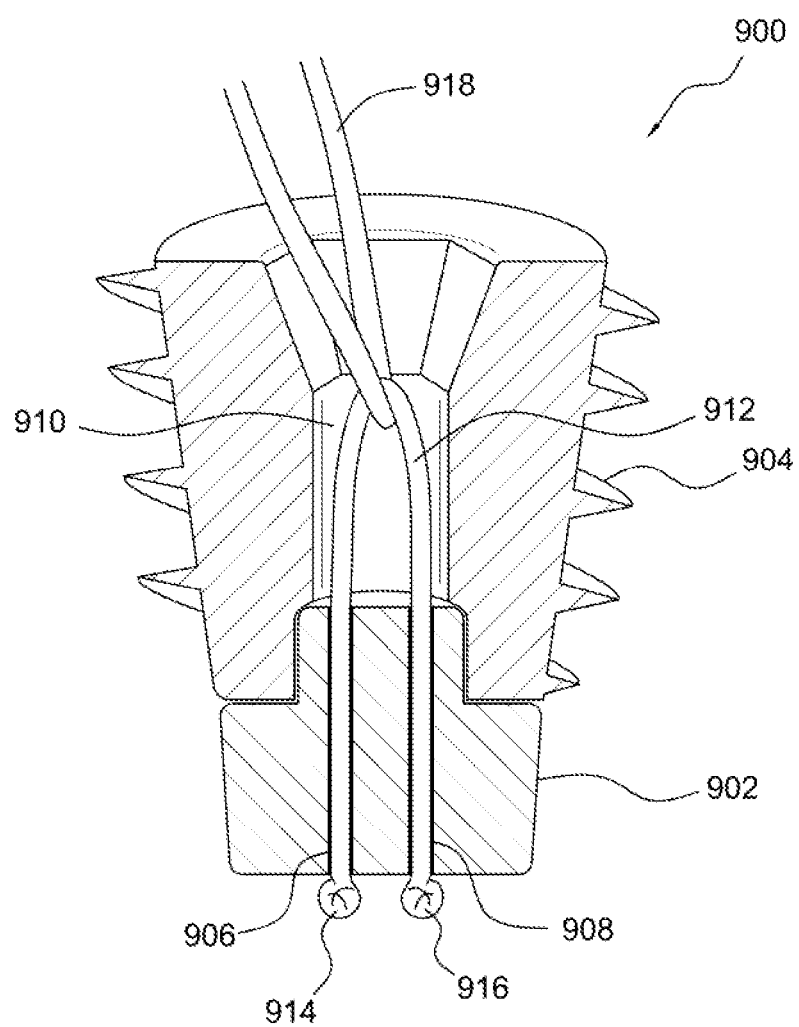
FIG. 9 shows, in cross-section, a suture loop according to one embodiment of the invention.

FIG. 9 shows, in cross-section, a portion of anchor 900 including a suture loop according to one embodiment of the invention. As shown, the anchor includes a stopper portion 902 and a fixing portion 904. The stopper portion 902 includes first 906 and second 908 longitudinal bores that, when the stopper portion 902 is disposed adjacent to the fixing portion 904, open onto a longitudinal bore 910 of the fixing portion 904. A first length of suture 912 is adapted to be knotted 914 at first end, to pass through the first stopper portion bore 906 into the fixing portion bore 910 and back through the second stopper portion bore 908.

A further knot 916 is adapted to retain the first length of suture 912 in place in the illustrated suture loop configuration. A portion of a further length of suture material 918 is disposed within the bore 910 and engages with the first length of suture 912 as shown. As will be understood by one of ordinary skill in the art, an interface between the surfaces of the first 912 and second 918 lengths of suture material will exhibit desirably low friction. Further, the illustrated arrangement serves to couple the length of suture 918 effectively in relation to the anchor 900.

Figure 10:
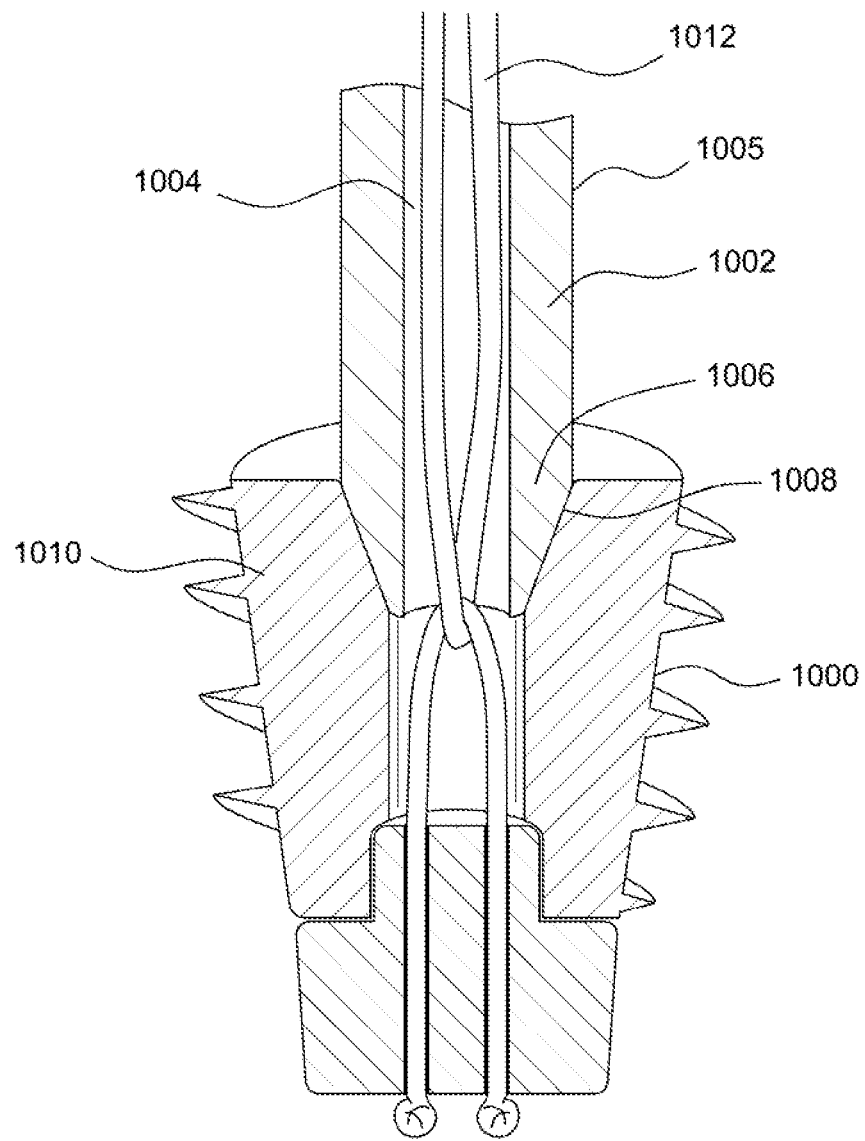
FIG. 10 shows, in cross-section, a portion of an anchor device and an insertion tool according to one embodiment of the invention.

FIG. 10 shows, in cross-section, a portion of a combination of an anchor 1000 with an insertion tool 1002. In the illustrated embodiment, the insertion tool 1002 includes a shaft portion 1005 having a longitudinal internal bore 1004 (i.e., a cannulated shaft). As shown, a distal portion 1006 of the shaft portion 1005 is adapted to engage with a tool engagement region 1008 of a fixing portion 1010 of anchor 1000. As a consequence of this arrangement, the fixing portion 1010 is adapted to receive a force such as a torque, transmitted by the shaft portion 1005.

As shown, the longitudinal bore 1004 of the shaft portion 1005 is adapted to receive a length of suture 1012 therewithin. This arrangement allows the shaft portion 1005 to engage with the tool engagement region 1008 without interference from the length of suture 1012. In certain embodiments of the invention, a kit is provided including an anchor having a stopper portion with a suture loop and a further length of suture, a fixing portion, and an insertion tool, all packaged together as a preassembled unit.

It should be noted that the various anchors illustrated and discussed above exhibit a variety of surface features including helical thread features and circular barb features and interrupted helical and circular barb features. In various embodiments of the invention particular features are selected for engagement with a particular substrate. Thus in one embodiment of the invention, an anchor is provided with a surface feature adapted to engage advantageously with cortical bone tissue.

In another embodiment, an anchor is provided with a surface feature adapted to engage with cancellous bone tissue. In certain other embodiments of the invention, a single anchor device may include surface features adapted to engage different substrates. Thus in one embodiment, an anchor is provided having a first surface feature adapted to engage cortical bone and a second surface feature adapted to engage cancellous bone tissue.

According to a further embodiment of the invention, it is advantageous to provide a stopper portion adapted to be substantially fixedly coupled to a corresponding fixing portion of a bone anchor. Such a fixing coupling can be advantageous both in terms of keeping the stopper portion and the fixing portion together during insertion of a bone anchor and also in terms of providing a robust coupling between the anchor and surrounding substrate, such as bone tissue.

Figure 11:
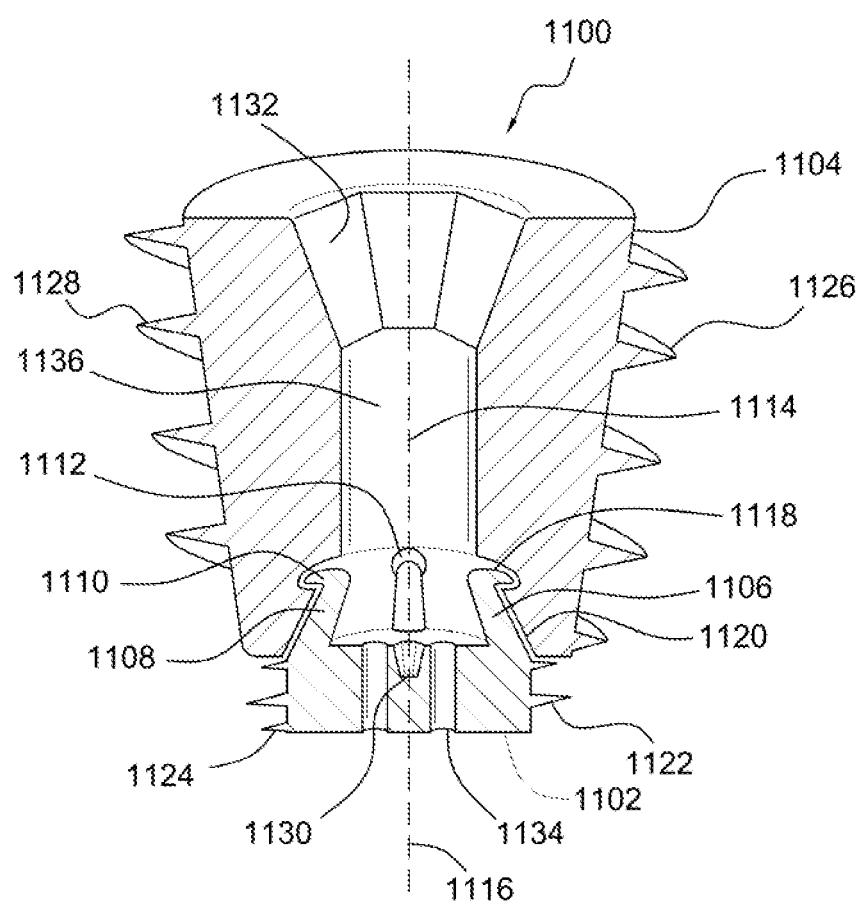
FIG. 11 shows, in cross-section, a portion of an anchor device including a stopper portion, a fixing portion and a detent mechanism, according to one embodiment of the invention.

FIG. 11 shows, in cross-section, a further embodiment of an anchor 1100. Anchor 1100 includes a first stopper portion 1102 and a second fixing portion 1104. Advantageously, the anchor 1100 includes a detent device 1106 adapted to substantially fixedly couple stopper portion 1102 to fixing portion 1104. In the embodiment illustrated as anchor 1100 the detent device 1106 includes a plurality of quasi-elastic arms (e.g., 1108) supporting a respective plurality of barbed hooks (e.g. 1110) or barbs. The arms 1108 are, in certain embodiments, coupled to or integral with stopper portion 1102. Each hook 1110 is adapted to be received within a corresponding cavity (e.g., 1112). Cavity 1112 opens into bore 1114 within fixing portion 1104.

Following a method according to one embodiment of the invention, stopper portion 1102 and fixing portion 1104 are aligned substantially coaxially along a longitudinal axis 1116. Forces are applied that urge stopper portion 1102 and fixing portion 1104 to move into proximity, each relative to the other. As this motion proceeds, proximal surface regions 1118 of barbs 1110 interfere mechanically with oblique surface regions 1120 of the fixing portion 1104. This mechanical interference motivates a pivotal deflection of the arms 1108 with respect to stopper portion 1102, moving the barbs 1110 progressively towards longitudinal axis 1116. This trend proceeds until the barbs 1110 reach the cavities 1112, whereupon elastic forces exerted by the arms move the barbs 1110 into the cavities 1112. Thereafter, the same elastic forces tend to retain barbs 1110 within cavities 1112.

One of skill in the art will appreciate that this arrangement tends to retain the stopper portion 1102 and fixing portion 1104 in substantially fixed relation to one another. In particular, it should be noted that the illustrated arrangement inhibits both further linear motion along the longitudinal axis 1116 with respect to one another and rotary motion of the stopper portion and fixing portion around longitudinal axis 1116 with respect to one another.

According to one embodiment of the invention, the stopper portion 1102 and fixing portion 1104 are urged together coaxially during assembly of an anchor device. As in the case of embodiment 1100, however, assembly of the stopper portion 1102 to the fixing portion 1104 is advantageously performed in situ within substrate tissue.

Accordingly, in one aspect of the invention, the illustrated stopper portion 1102 includes a first externally threaded surface feature 1122 including a substantially helical surface ridge 1124. It should be noted that first externally threaded surface feature 1122 is configured as a left-handed thread. The fixing portion 1104 includes a second externally threaded surface feature 1126 including a substantially helical surface ridge 1128. It should be noted that second externally threaded surface feature 1126 is configured as a right-handed thread. One of skill in the art will appreciate that the handedness identified above is merely exemplary and is readily reversed in alternative embodiments of the invention so that the stopper portion includes a right-handed thread and the fixing portion includes a left-handed thread.

According to one embodiment the invention includes a method of inserting a first anchor portion by a left-handed rotation of the stopper portion so as to screwingly advance the stopper portion within a substrate; and thereafter inserting a fixing portion by a right-handed rotation of the fixing portion so as to screwingly advance the fixing portion within the substrate. According to one aspect of the invention as the fixing portion arrives in proximity to the stopper portion a substantially permanent coupling between the two anchor portions is made, whereupon the opposite threading of the two portions serves to substantially limit further rotation of either anchor portion of the combined anchor portion assembly.

In light of the here-described method it should be noted that, according to one embodiment, stopper portion 1102 includes a first receiving feature 1130 adapted to receive a first portion of a first insertion tool, and fixing portion 1104 includes a second receiving feature 1132 adapted to receive a second portion of a second insertion tool. It should be noted, however, that in certain embodiments, receiving portions can be configure so that a single insertion tool can be used in relation to both a stopper portion and a fixing portion. Although not shown, one of skill in the art will readily understand that a suture loop arrangement, as described above, can be disposed in relation to the illustrated bores 1134, 1136 of anchor 1100.

Figure 12:
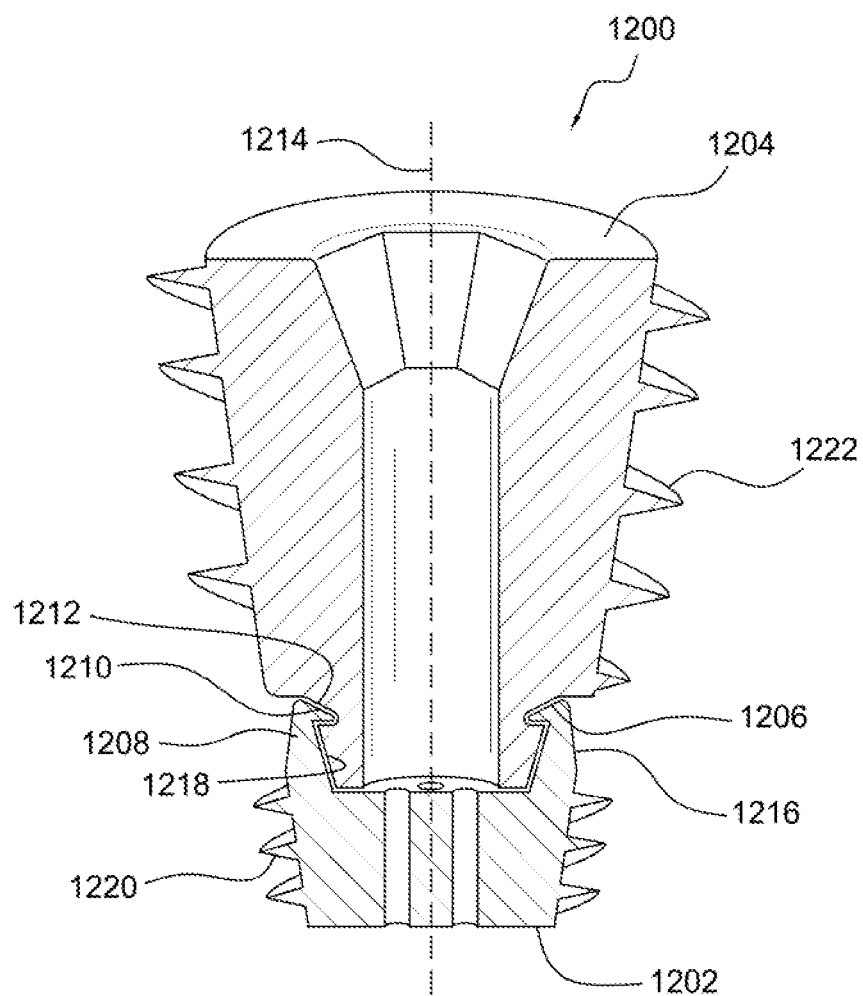
FIG. 12 shows, in cross-section, an anchor device according to a further embodiment of the invention.

FIG. 12 shows, in cross-section, a portion of a further embodiment of an anchor 1200 including a stopper portion 1202 and a fixing portion 1204. The anchor 1200 includes a detent device 1206. In the illustrated embodiment, detent device 1206 includes at least one reasonably flexible arm 1208 having a barbed hook portion 1210. The barbed hook 1210 is adapted to be received within a corresponding cavity 1212 of fixing portion 1204. It should be noted that, during an assembly process, reasonably flexible arm 1208 is adapted to be deflected outwardly away from longitudinal axis 1214 by interference between a first surface region 1216 of barbed hook portion 1210 and a corresponding external surface region 1218 of fixing portion 1204.

One of skill in the art will observe that whereas arm 1108 of anchor 1100 is deflected during assembly inwardly towards longitudinal axis 1116 and then relaxes hook 1110 outwardly into an internal cavity 1112 of fixing portion 1104, arm 1208 of anchor 1200 is deflected during assembly outwardly away from longitudinal axis 1214 and then relaxes inwardly into an external cavity 1212 of fixing portion 1204. In both illustrated embodiments 1100 and 1200, interfering surfaces 1120 and 1218 exhibit substantially circular symmetry about respective longitudinal axis 1116, 1214 and are disposed generally obliquely with respect to the respective longitudinal axes. It should be noted that, in various embodiments, these interfering surfaces may exhibit simple and/or compound curvature.

As with the embodiment of anchor 1100, anchor 1200 includes opposing left-handed threads 1220 and right-handed threads 1222 so that once the stopper portion 1202 and fixing portion 1204 are assembled in situ within a substrate, and decent portion 1206 is activated to lock the two portions together, the opposing threads tend to prevent further rotation and other motion of the completed assembly.

It should be noted that, in certain embodiments, a first, relatively narrow, receiving hole is bored in a substrate to receive the stopper portion. In some embodiments, this receiving hole is in advance of insertion of the stopper portion. In other embodiments, the stopper portion includes a self-tapping thread. In still other embodiments, the stopper portion includes a self-punching self-tapping thread adapted to allow insertion of the stopper portion without the pre-drilling of a receiving hole. In certain embodiments no receiving hole is predrilled, but a lead hole of substantially smaller diameter than the stopper portion is predrilled in the substrate.

In other embodiments, a receiving hole is drilled that includes a relatively narrow diameter portion adapted to receive the stopper portion and a relatively wider diameter portion adapted to receive the fixing portion of the anchor. According to certain methods of the invention, a plural-diameter hole is prepared in a single operation using an appropriate tool of stepped diameter. Likewise, an appropriate tool may be used to simultaneously drill and tap a receiving hole of a single or of a plural diameter.

Figure 13:
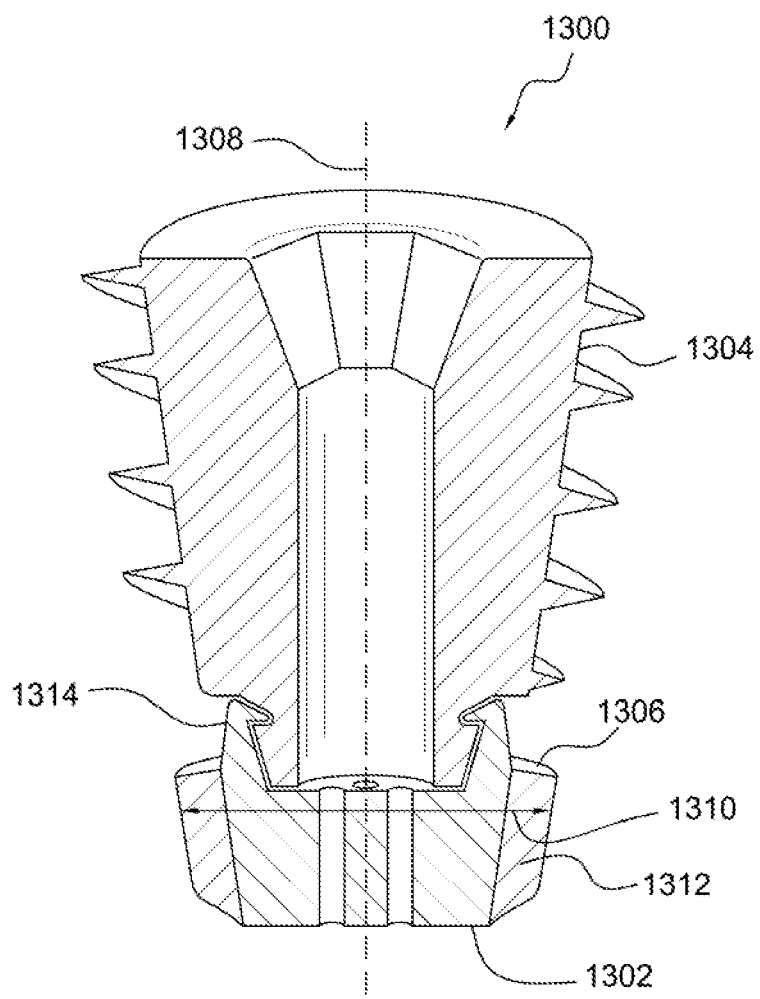
FIG. 13 shows, in cross-section, an anchor device according to another embodiment of the invention.

FIG. 13 shows an anchor 1300 including a stopper portion 1302 and a fixing portion 1304. The stopper portion 1302 includes one or more substantially radially projecting vanes 1306. The vanes 1306 are adapted to prevent rotation of stopper portion 1302 about a longitudinal axis 1308 when the stopper portion 1302 is disposed within a substrate matrix such as, for example, osseous tissue.

According to one method within the scope of the invention, an appropriately sized receiving hole is prepared in a region of substrate bone tissue. The receiving hole is configured to have a diameter appropriately less than a corresponding diameter 1310 across the vanes 1306 of stopper portion 1302. Stopper portion 1302 is disposed coaxially at a mouth of the receiving hole and urged along longitudinal axis 1308 into the receiving hole. According to one embodiment of the invention, vanes 1306 are adapted to cut into, or otherwise displace, a portion of the substrate bone disposed radially with respect to the receiving hole as the stopper portion 1302 is advanced into the receiving hole. Consequently, when the stopper portion 1302 has been sufficiently received into the receiving hole as rotation about longitudinal axis 1308 is substantially inhibited by a mechanical interference between external surfaces (e.g. 1312) of the vanes and the surrounding substrate.

Thereafter, fixing portion 1304 is advanced with rotation into the receiving hole until a detent mechanism 1314 engages. Thereafter, the mechanical engagement between the stopper portion 1302 and the fixing portion 1304, in combination with the action of the vanes 1306 to inhibit rotation of the stopper portion 1302 serves to substantially prevent undesirable counter-rotation and consequent withdrawal of the fixing portion 1304.

Figure 14:
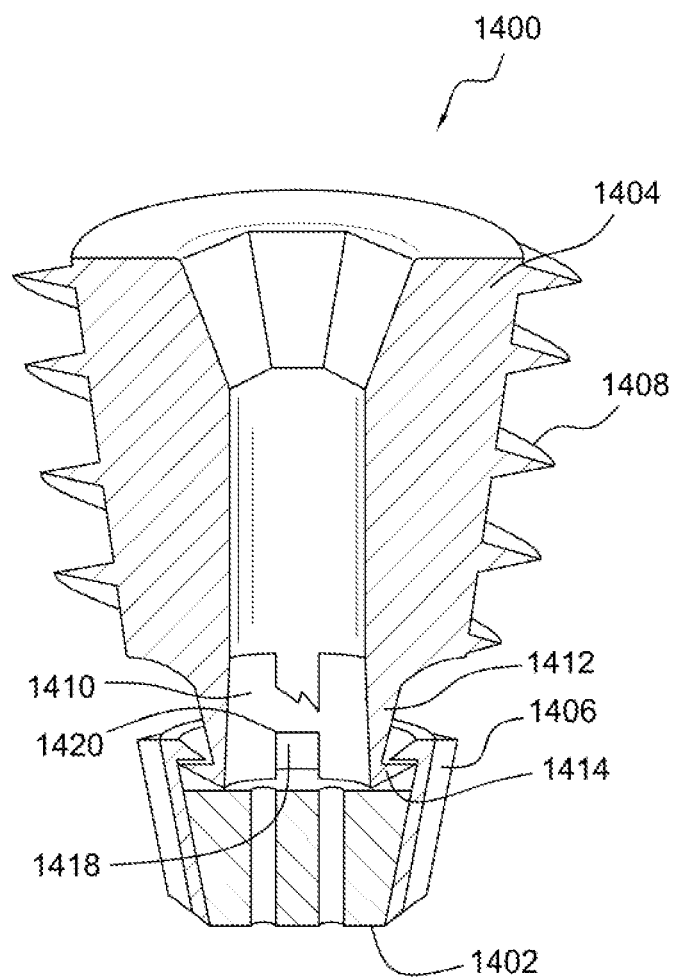
FIG. 14 shows, in cross-section, art anchor device according to still another embodiment of the invention.

FIG. 14 shows a further embodiment of an anchor 1400 according to principles of the invention. The anchor 1400 includes a stopper portion 1402 and a fixing portion 1404. The stopper portion 1402 has at least one anti-rotation vane 1406. The fixing portion 1404 has an external surface thread feature 1408. A detent mechanism 1410 includes a plurality of substantially flexible arms 1412 that are integral with or coupled to fixing portion 1404. The arms 1412 include respective barbed hooks 1414 adapted to be received internally within stopper portion 1402.

Figure 15:
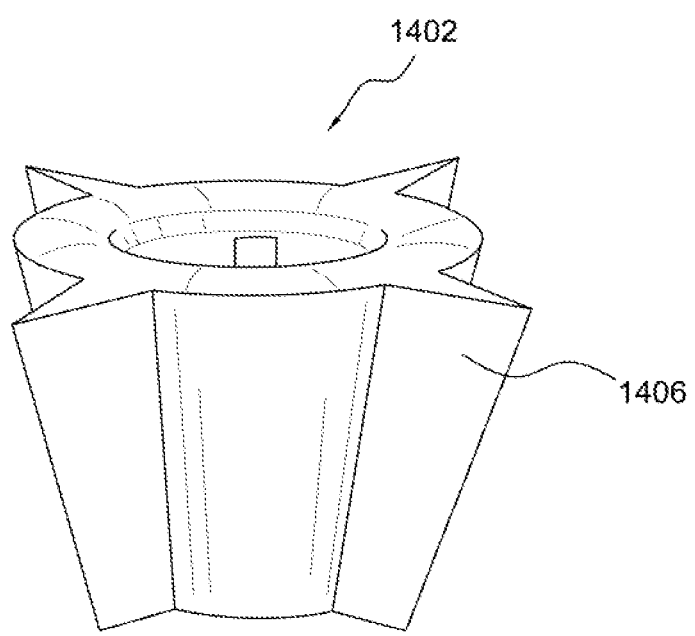
FIG. 15 shows, in perspective view, a stopper having an anti-rotation vane according to one embodiment of the invention.

FIG. 15 shows a further perspective view of stopper 1402 including four illustrative vanes 1406.

Figure 16:
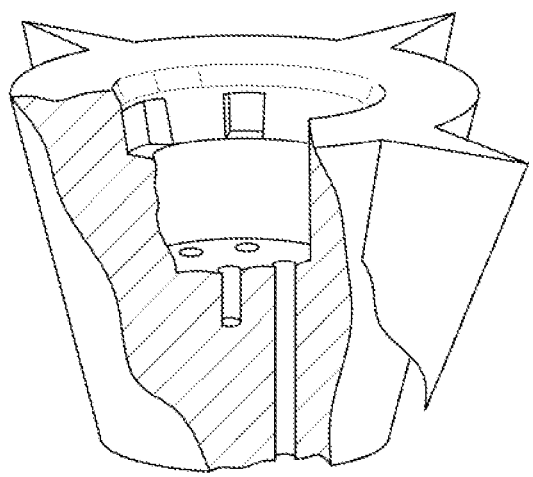
FIG. 16 shows, in cutaway perspective view, a stopper according to one embodiment of the invention.

FIG. 16 shows a further cutaway view of stopper 1402. In the illustrated embodiment, stopper portion 1402 includes a plurality of receiving cavities 1418 adapted to receive and retain the barbed hooks 1414 (FIG. 14). The illustrated receiving cavities have a substantially rectangular circumferential profile 1420, however alternative profiles including, without limitation, circular, triangular, polygonal and curved are contemplated. In addition, it is anticipated that the number of receiving cavities 1418 may differ from a number of barbed hooks 1414. For example, there may be more receiving cavities than barbed hooks or more barbed hooks than receiving cavities.

Figure 17:
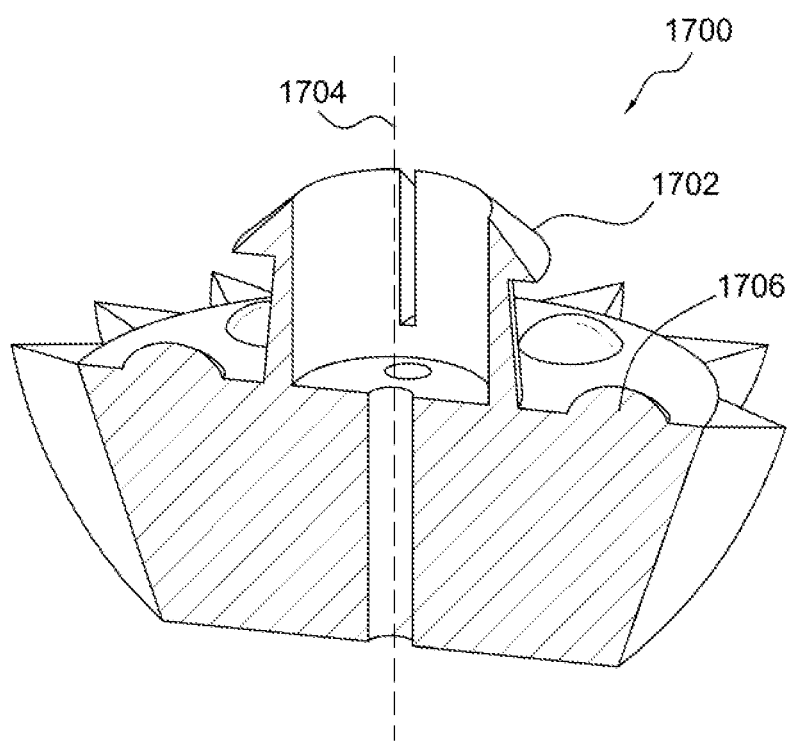
FIG. 17 shows, in quasi-cross-sectional view, a stopper including a detent mechanism according to one embodiment of the invention.

It should be understood that the above-described barbed hooks are merely exemplary of a wide variety of other detent mechanisms that are contemplated within the scope of the invention. Thus, FIG. 17 shows a stopper 1700 according to a further embodiment of the invention including a first barbed-hook detent feature 1702 adapted to prevent linear withdrawal of a fixing portion (not shown) along longitudinal axis 1704 with respect to stopper 1700. A separate hemispherical detent feature 1706 is adapted to be received within a corresponding cavity of the fixing portion to inhibit rotation about longitudinal axis 1704 of the fixing portion with respect to the stopper portion 1700.

Figure 18:
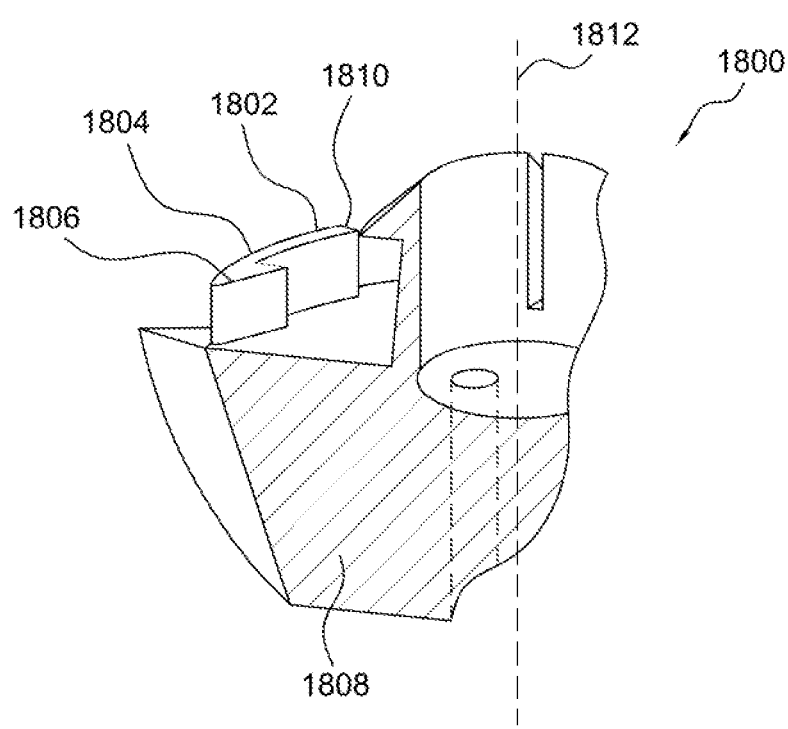
FIG. 18 shows, in cutaway perspective view, a stopper including a detent mechanism according to another embodiment of the invention.

It will be appreciated that, while detent feature 1706 is shown as a substantially hemispherical projection, well adapted to be received in a corresponding substantially concave hemispherical recess of a fixing portion, alternative arrangements are possible. For example a concave recess may be provided on the stopper portion while a corresponding convex projection may be provided on the fixing portion. Likewise, each of the stopper portion and the fixing portion may include both convex and concave features. Further, the hemispherical shape of the projection is merely illustrative of a wide variety of possible shapes and configurations that fall within the scope of the invention in its various embodiments. Thus, for example, FIG. 18 shows a portion of a stopper 1800 including an anti-rotation detent feature 1802 having a generally flexible arm 1804 and a barbed hook 1806 at one end thereof.

The generally flexible arm 1804 is integral with or coupled to a body 1808 of the stopper portion 1800 at an end 1810 opposite to the barbed hook 1806. In the illustrated embodiment, the arm 1804 is adapted to deflect, so as to allow the barbed hook 1806 to be displaced generally radially outward with respect to longitudinal axis 1812. Thereafter, the arm 1804 is adapted to resile so as to position a portion of the barbed hook 1806 within a corresponding cavity of a fixing portion (not shown). Consequently, as will be understood by one of skill in the art, the fixing portion and stopper portion 1800 are adapted to be locked in substantially fixed spatial relation to one another and to a surrounding substrate.

Figure 19:
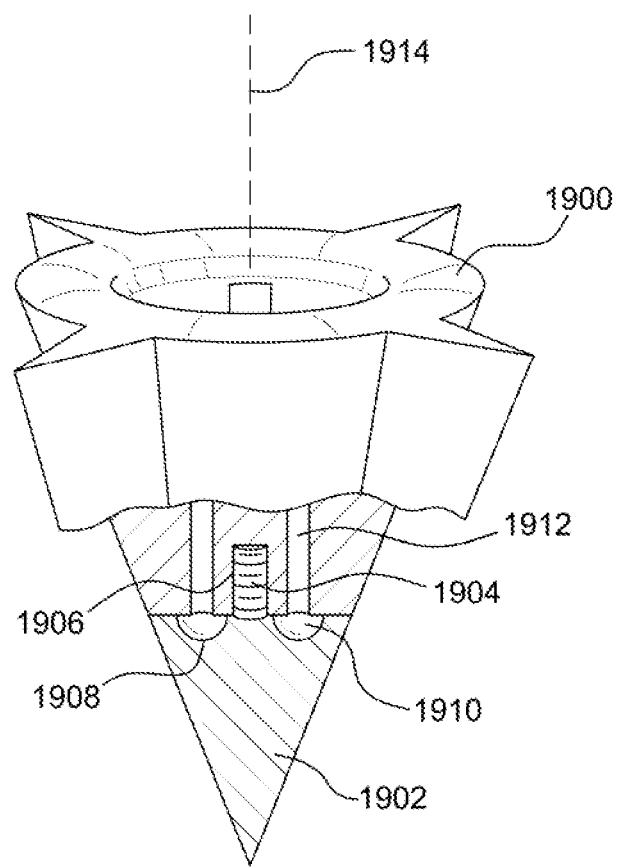
FIG. 19 shows, in cutaway perspective view, a stopper including a piercing point according to one embodiment of the invention.

FIG. 19 shows, in cutaway cross-sectional view, a stopper portion 1900 according to a further embodiment of the invention. The stopper portion 1900 is adapted to be coupled to an exemplary piercing point 1902. In the illustrated embodiment, the piercing point includes a fastener, shown here for example as an externally threaded stud 1904, adapted to be received within an internally threaded bore 1906 of the stopper 1900. In the illustrated embodiment, the piercing point includes an annular cavity or channel 1908 adapted to accommodate a knot 1910 of a suture loop (not shown).

While the piercing point 1902 is shown here as a discrete component adapted to be assembled to stopper portion 1900, one of skill in the art will appreciate that stopper 1900 could equally well be prepared to include an integral piercing point. In the case of a stopper having an integral piercing point, suture channels (e.g., 1912) can be configured to exit the stopper longitudinally and/or radially with respect to a longitudinal axis 1914 of the stopper 1900.

It should also be understood that the stopper and piercing point can be made of the same or differing materials according to the requirements of a particular embodiment and application.

Thus, in one embodiment a fixing portion, a stopper portion, and a piercing point may each be made of any one of a biocompatible material including natural and synthetic polymers such as, for example, poly-ether-ether-ketone (PEEK); reinforced polymer materials including reinforcing sheets and/or particles and/or fibers of, for example, one or more of, carbon fibers, carbon nano-materials, glass fibers and metallic fibers; precious metals, stainless steel, titanium and other metals; porcelain, alumina and other ceramics including, for example, aluminum oxide, calcium oxide, calcium phosphate hydroxyapatite, and zirconium, and combinations thereof.

Figure 20:
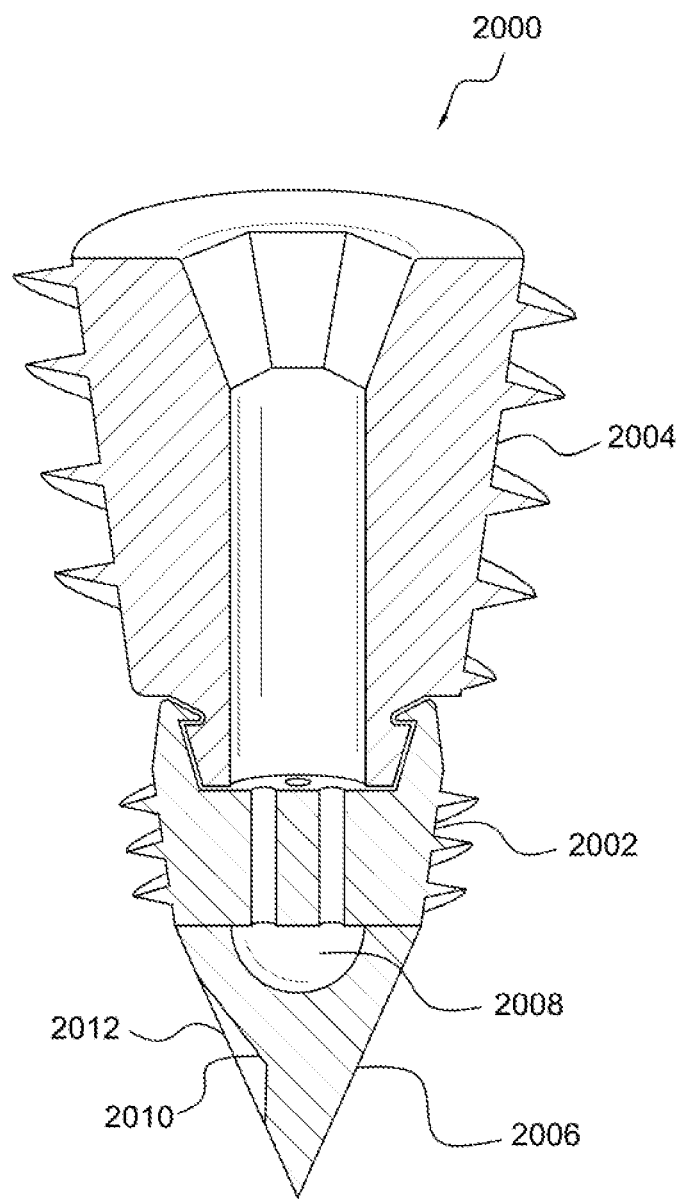
FIG. 20 shows, in cross-section, an anchor according to one embodiment of the invention.

FIG. 20 shows an anchor 2000 according to a further embodiment of the invention. Anchor 2000 includes a first stopper portion 2002 and a second fixing portion 2004. The stopper portion 2002 includes a piercing point 2006. According to one embodiment of the invention, piercing point 2006 includes a cavity 2008, here shown as a generally hemispherical cavity adapted to receive a suture knot therewithin. The exemplary piercing point illustrated here also has a depressed region 2010 and a cutting edge 2012 adapted to facilitate a substrate piercing function of the piercing point 2006.

Figure 21:
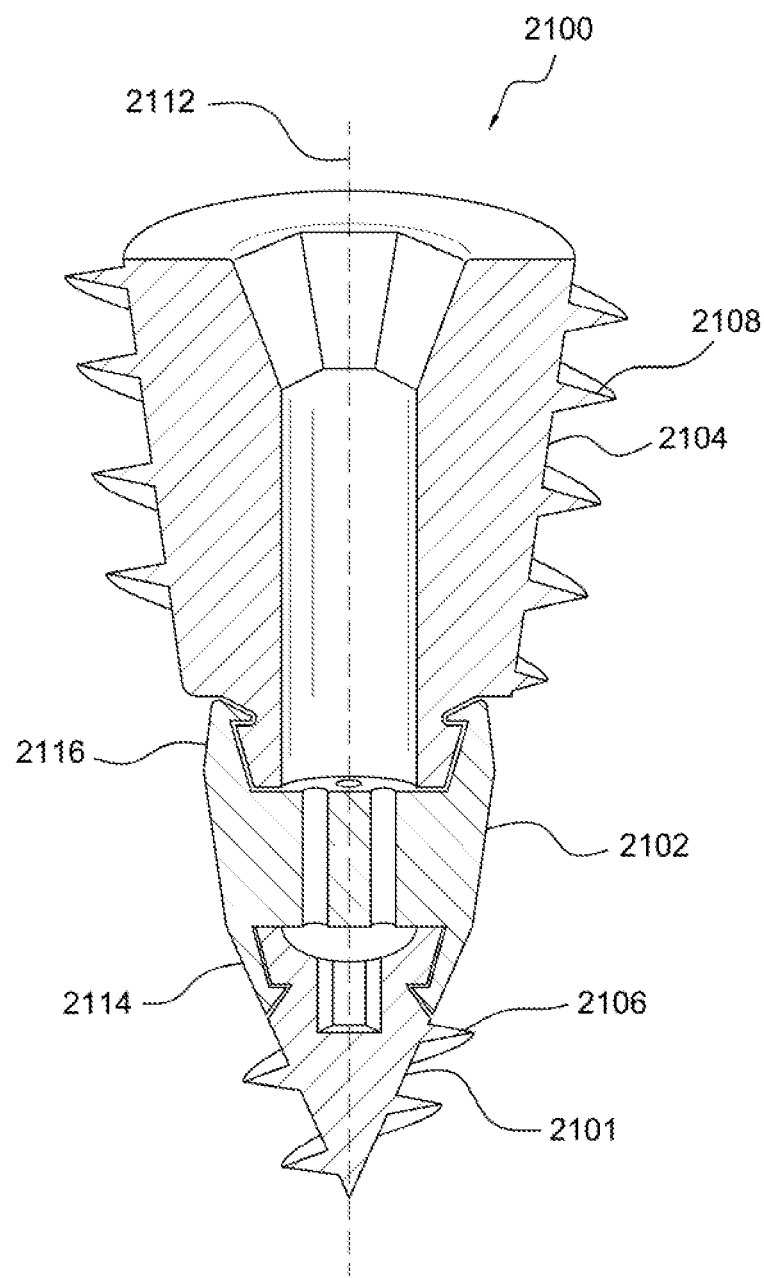
FIG. 21 shows, in cross-section, an anchor according to another embodiment of the invention.

FIG. 21 shows, in cross section, an anchor 2100 according to a further embodiment of the invention. Anchor 2100 includes a first piercing point 2101, a second stopper portion 2102, and a third fixing portion 2104. As shown, the piercing point 2101 includes a first surface feature, here shown as left-handed threads 2106. The fixing portion 2104 includes a second surface feature, here shown as right-handed threads 2108. In the presently illustrated embodiment, the stopper portion 2102 does not include a surface feature adapted to prevent rotation or withdrawal along longitudinal axis 2112 of the stopper portion 2102. The stopper portion 2102 does include, however, detent devices 2114, 2116, adapted to substantially fixedly couple the stopper portion 2102 to the piercing point 2101 and the fixing portion 2104 respectively.

It should be appreciated that in other embodiments, the stopper portion includes an anti-rotation or anti-extraction surface feature such as a plurality of vanes. In other embodiments, one or more of the piercing point 2101 and the fixing portion 2104 includes an alternative anti-rotation or anti-extraction surface feature such as, for example, a plurality of vanes.

Figure 22:
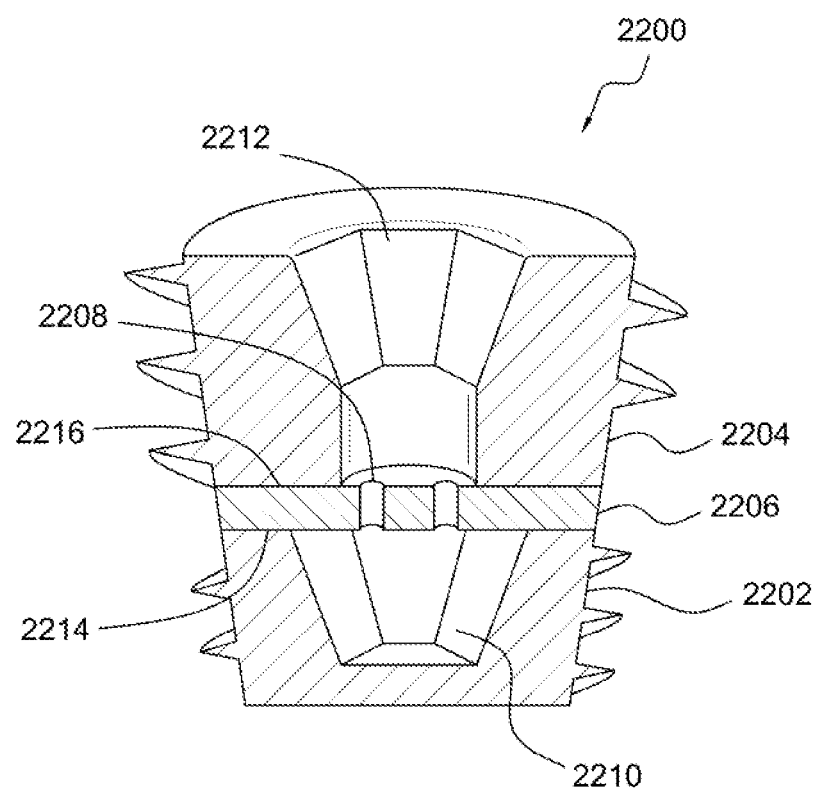
FIG. 22 shows, in cross-section, an anchor according to still another embodiment of the invention.

FIG. 22 shows, in cross section, a further anchor 2200. Anchor 2200 includes a first stopper portion 2202, a second fixing portion 2204, and a retainer portion 2206. The retainer portion 2206 includes at least one longitudinal bore 2208 adapted to receive a portion of a suture therewithin. As illustrated, the stopper portion 2202 includes a surface feature, here shown as left-handed threads, for example. The fixing portion 2204 includes a surface feature, here shown as right-handed threads, for example. Both the stopper portion 2202 and in the fixing portion 2204 include respective tool receiving features 2210, 2212. In one embodiment, the retainer portion 2206 includes a contact surface 2214 adapted to engage a corresponding surface of stopper portion 2202.

In the illustrated embodiment, the retainer portion 2206 also includes a contact surface 2216 adapted to engage a corresponding surface of fixing portion 2204. According to one embodiment of the invention, contact surfaces 2214 and 2216 are adapted to frictionally engage corresponding surfaces of the stopper portion 2202 and fixing portion 2204. In other embodiments, the anchor 2200 is adapted to receive, for example, a chemical adhesive material, at surfaces 2214 and 2216. In still other embodiments, the anchor 2200 is adapted to be treated after insertion into a substrate to form a physical bond at surfaces 2214 and 2216. For example, one or more of a thermal weld and an ultrasonic weld may be formed at surfaces 2214 and 2216 to prevent decoupling of the stopper portion 2202 from the fixing portion 2204 and the retainer portion 2206.

Figure 23:
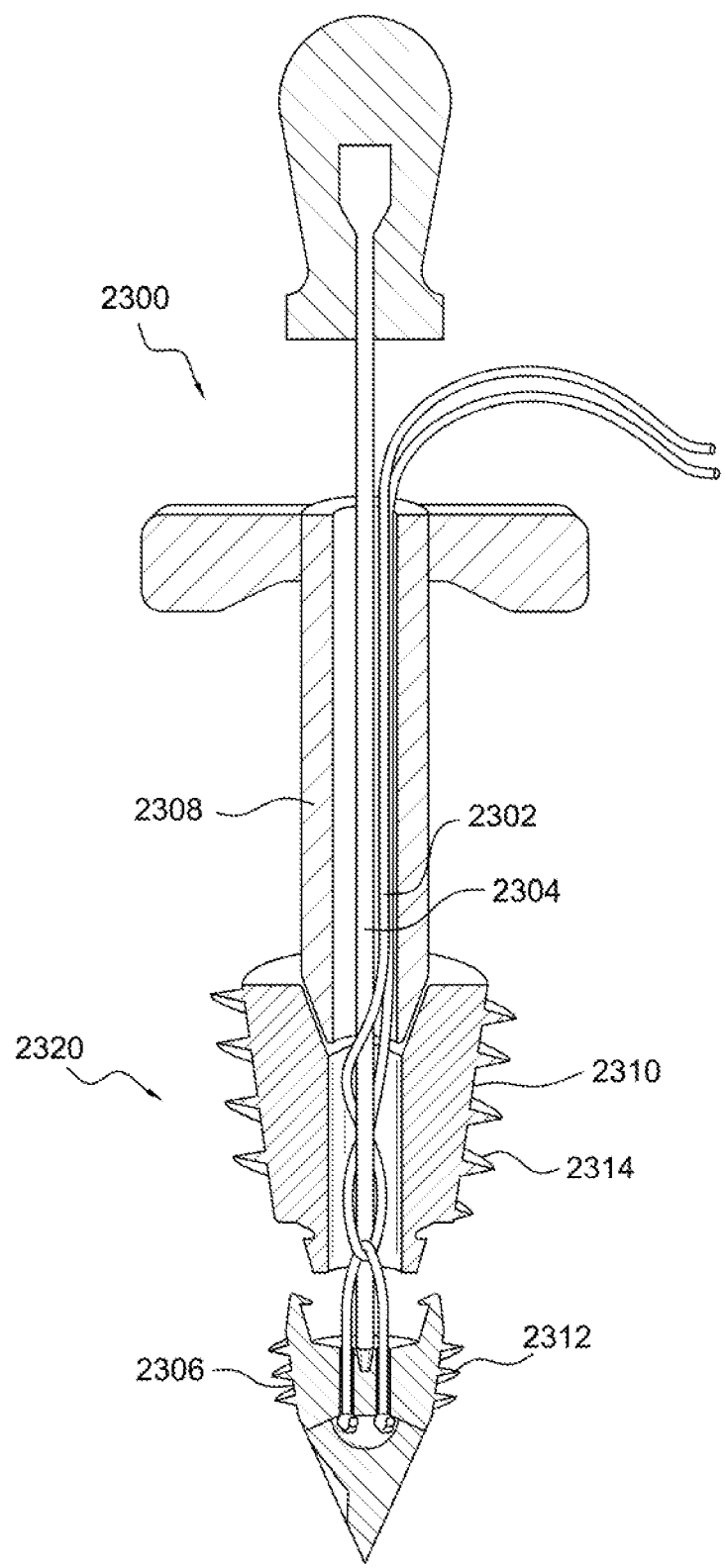
FIG. 23 shows in cross-section, a portion of an anchor and insertion tool kit according to one embodiment of the invention.

One of skill in the art will appreciate that a variety of methods are evident from the above-provided description and included within the scope of the present invention as disclosed. Thus, according to one method of the invention, a first hole is drilled or pierced into a substrate such as a bone. A cannulated insertion tool 2300, as shown in FIG. 23 has a suture 2302 disposed generally longitudinally adjacent to a first substantially solid shaft 2304 thereof. The first shaft 2304 is used to drive a self-tapping stopper portion 2306 into the hole by a leftward rotation of the first shaft 2304. Subsequently, a further portion of the cannulated insertion tool, including a second cannulated shaft 2308 coaxially encircling the first substantially solid shaft 2304 is used to drive a self-tapping fixing portion 2310 into the hole by a rightward rotation of the second shaft 2308 until the stopper portion 2306 and the fixing portion 2310 engage and lock together. Thereafter the opposing sense of the threads 2312, 2314 of the stopper portion and of the fixing portion respectively prevent subsequent rotation and withdrawal of the resulting anchor assembly 2320.

Figure 24:
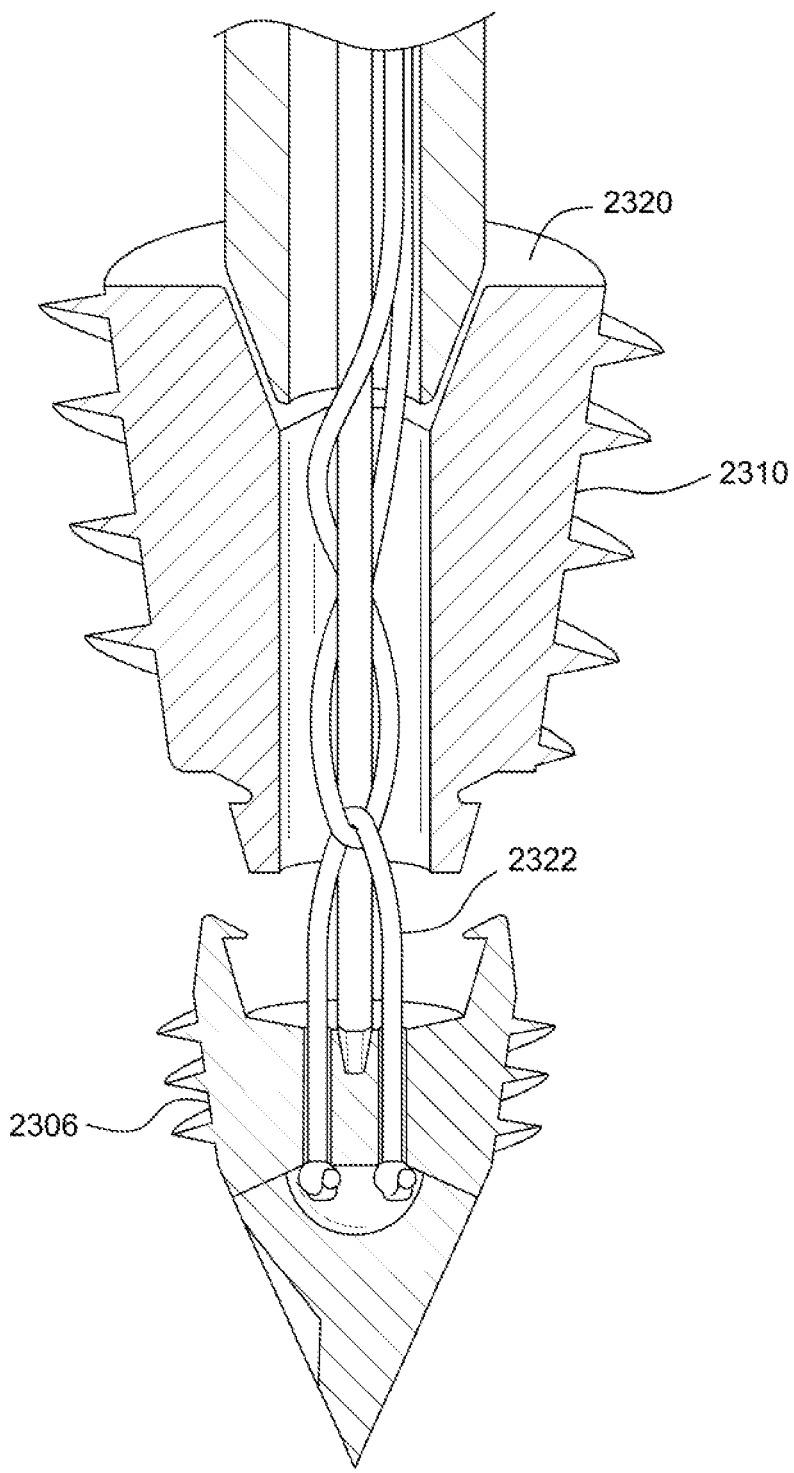
FIG. 24 shows, in cross-section, a portion of an anchor and insertion tool kit as used in a method according to one embodiment of the invention.

FIG. 24 shows the relationship of the stopper portion 2306, including suture loop 2322 and fixing portion 2310 in additional detail. In a typical application, the fixing portion 2310 will be installed in a substrate bone so that proximal surface 2320 is ultimately disposed substantially flush with an external surface of the bone.

In another embodiment of the invention, surface 2320 is ultimately disposed a short distance inwardly of the external surface of the bone. For example surface 2320 may be disposed between about 0 mm and at least about 0.5 mm below the external surface of the substrate bone. It should be further noted that in certain cases, elements of the anchor are tapped, pounded and/or pressed into place, rather than rotated into place.

One of skill in the art will appreciate that a threaded suture anchor can be deployed into cortical bone. Purchase in cortical bone is enhanced by a narrow (e.g., approximately 1.5 mm) thread pitch. A wider thread pitch (e.g., approximately 3 mm) is advantageously deployed in cancellous bone. The push-in anchor has very broad application in areas such as the foot, the hand, and the shoulder. Advantageously, the push-in anchor has a compact size. This compact size is advantageous and allows for greater maneuverability in tight articular spaces.

Figure 25:
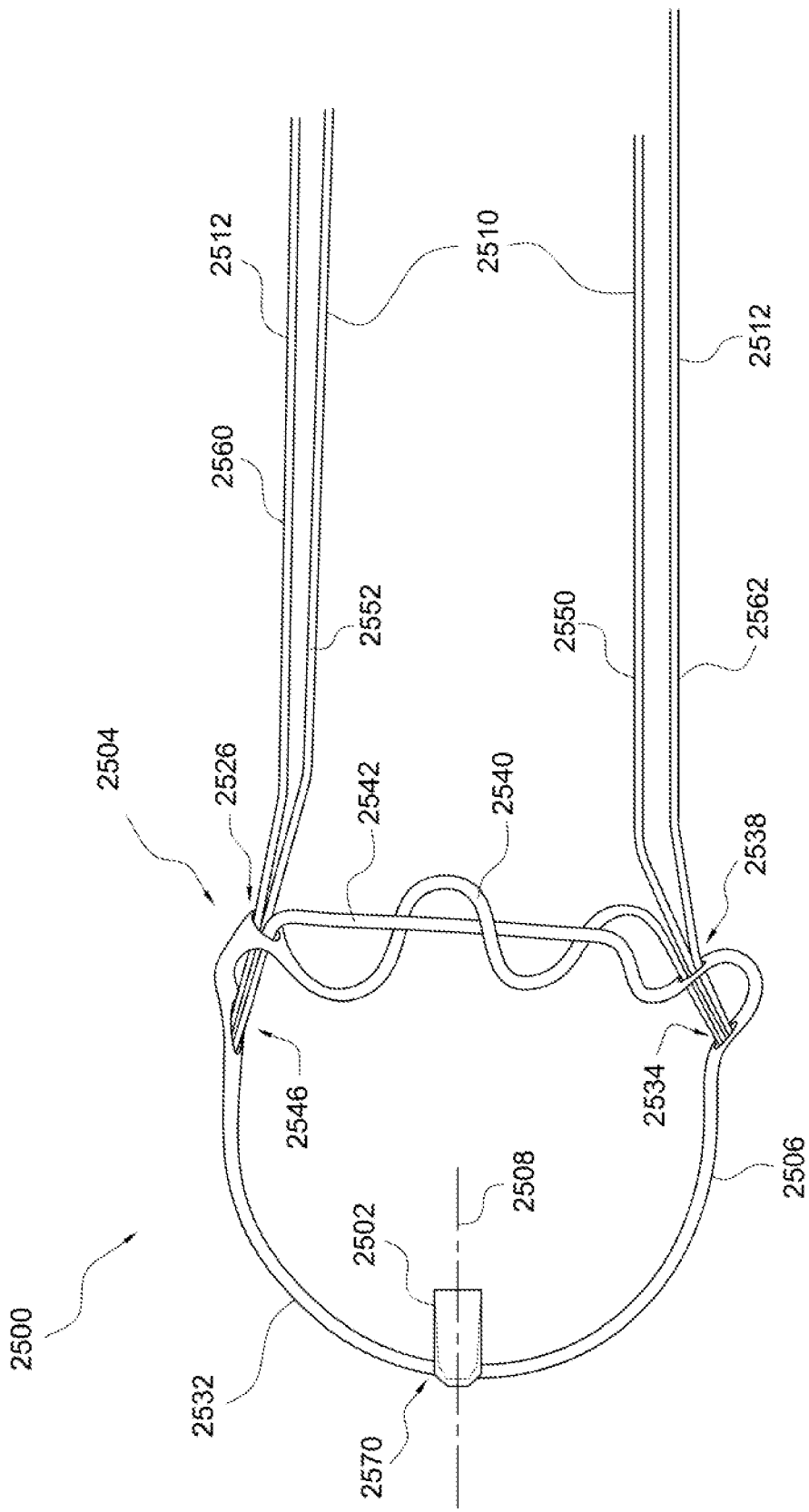
FIG. 25 shows, in schematic view, a portion of an anchor including a generally rigid stopper portion and a wadding portion.

FIG. 25 shows an anchor 2500 according to another embodiment of the invention. The anchor 2500 includes a first stopper portion 2502 and a second fixing portion 2504. The fixing portion 2504 of anchor 2500 includes a substantially flexible member 2506 structured so that, for example, under manual urging the flexible member 2506 transitions between a relaxed configuration and a constricted configuration. In the constricted configuration, the substantially flexible member 2506 of the fixing portion 2504 serves as a wadding that can be disposed in compression within a cavity. As will be further described below, the wadding or may or may not be knotted, depending on the requirements of a particular application. In various embodiments, the wadding serves to help fix a suture to a bone.

In certain embodiments, the stopper portion 2502 includes a substantially rigid member structured and configured for deployment within a bone cavity below a surface of a bone. According to requirements of a particular application, the stopper portion 2502 includes a structure arranged to facilitate its insertion within the bone cavity. In a further aspect, the stopper portion has a form arranged to promote retention of the anchor 2500 within the bone cavity. Preferably, the stopper portion 2502 leads the fixing portion 2504 into a bone cavity where the stopper portion and fixing portion cooperate to provide a surgical anchor point.

In the exemplary embodiment of FIG. 25, the anchor 2500 includes a stopper portion 2502 having a longitudinal axis 2508. The flexible member 2506 of the fixing portion 2504 includes a first deployment suture 2510 and a second sliding suture 2512. The deployment suture 2510 includes, in certain embodiments, a multi-stranded braided structure. In other embodiments, the deployment suture 2510 includes a generally tubular non-braided structure, where the term "generally tubular" indicates that at least a portion of the suture 2510 has an internal region through which a material object such as a further portion of the deployment suture 2510 can be moved.

Figure 26:
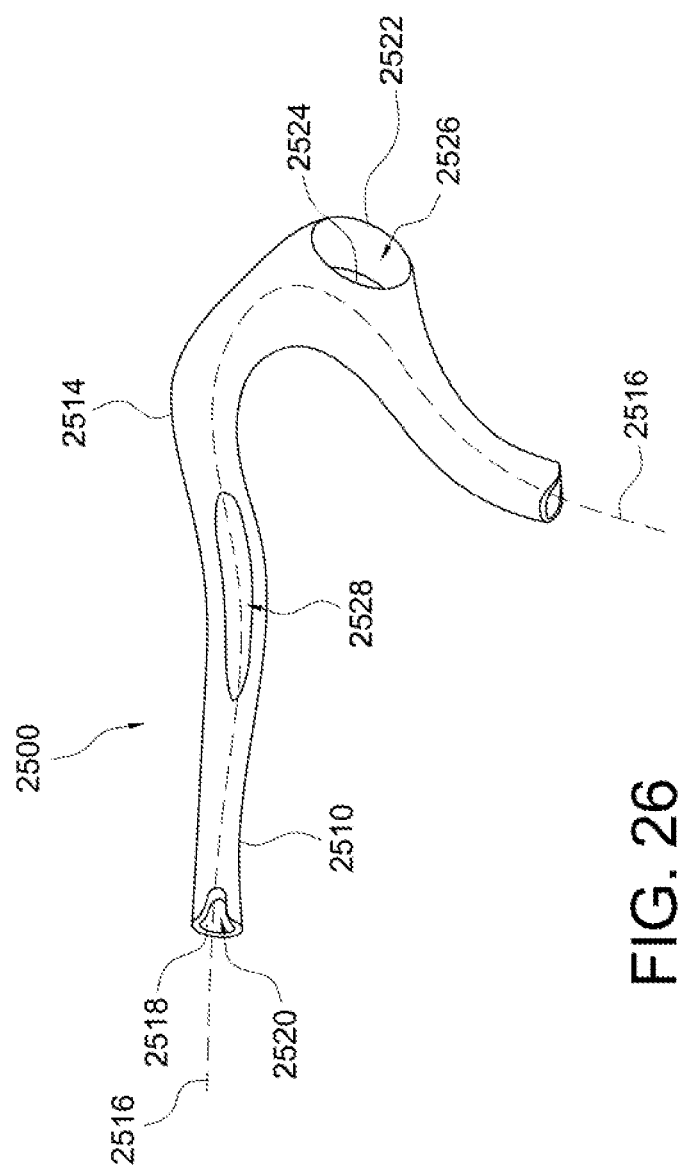
FIG. 26 shows, in schematic view, a further detailed portion of an anchor including a wadding portion.

FIG. 26 shows a portion of the deployment suture 2510 of anchor 2500 in additional detail, with certain portions of the deployment suture omitted for clarity. As shown, the deployment suture 2510 includes a generally tubular region 2514 defining a longitudinal axial curve 2516. An internal surface 2518 of the tubular region 2514 defines an axial cavity 2520 within the tubular region 2514 that is generally coincident with the curve 2516. It should be understood that in certain embodiments, the internal surface 2518 will be substantially smooth and well-defined whereas in other embodiments the internal surface 2518 will be defined by a plurality of sub-regions that may be more or less contiguous with one another, depending on the particular embodiment. Thus, for example, in an embodiment where the deployment suture 2510 includes an extruded polymer tube, the internal surface 2518 may be substantially smooth at the scale of the suture diameter.

On the other hand, in an embodiment where the deployment suture 2510 includes a braided fiber textile material, selected surface sub-regions of individual fibers may define a more or less abstract internal surface 2518 where the selected sub-regions of individual fibers are disposed adjacent to the axial cavity 2520 and together serve to define the abstract surface as an average of the individual sub-regions. Indeed, depending on the flexibility of the suture material, the suture may deform in such a way that the axial cavity 2520 tends to collapse completely or to the dimension of any inserted material.

As illustrated, tubular region 2514 exhibits first and second apertures 2522 and 2524 that, together, define a passage 2528 through the tubular region 2514. The passage 2526 is arranged generally transverse to axial curve 2516. In certain embodiments, the passage 2526 is substantially perpendicular to axial curie 2516. In other embodiments, the passage 2526 is disposed at an oblique angle with respect to axial curve 2518. In certain embodiments the apertures 2522 and 2524 are defined between corresponding regions of fiber material, where the fiber material is part of a braided textile suture material.

In certain embodiments, axial cavity 2520 extends to and/or beyond passage 2526 such that axial cavity 2520 intersects and is contiguous with passage 2526. In the illustrated embodiment, a further aperture 2528 defines an opening between axial cavity 2520 and an external environment of the deployment suture 2510.

Figure 27:
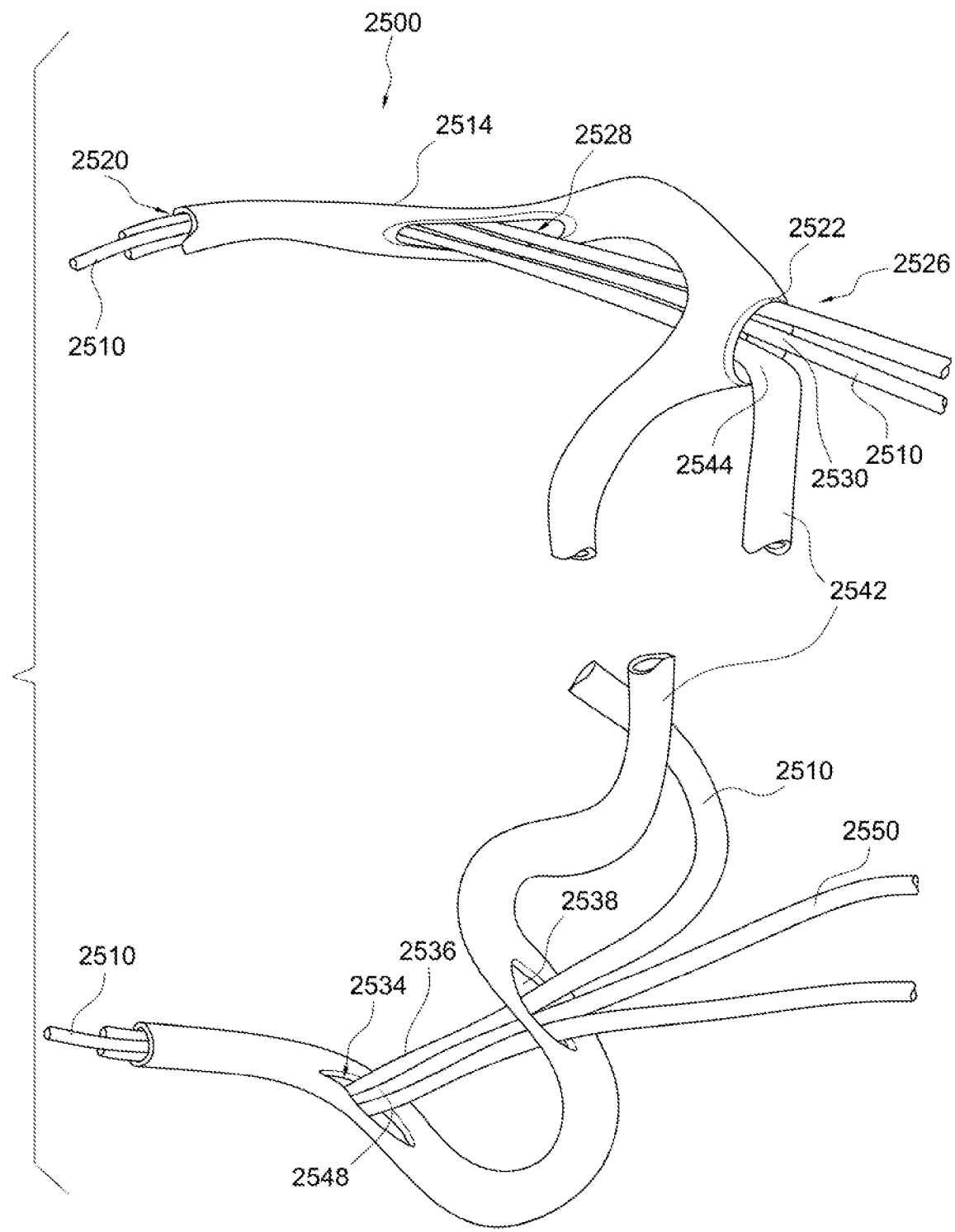
FIG. 27 shows, in schematic view, furthermore detail aspects of a portion of an anchor including a wadding portion.

FIG. 27 shows the tubular region 2514 discussed above in relation to FIG. 25 along with certain previously omitted additional features. As will be evident upon examining FIG. 25-27, the fixing portion 2504 includes coaxially looped sutures arranged to form a knot when deployment suture 2510 is pulled taut. Accordingly, a first portion 2530 of deployment suture 2510 is disposed within aperture 2522 and traverses passage 2526 emerging from the far end of the passage 2526 and entering through aperture 2528 into axial cavity 2520.

With reference to both FIGS. 25 and 27, deployment suture 2510 is disposed within axial cavity 2520 throughout circumferential region 2532 until it emerges from aperture 2534 adjacent to region 2536 of deployment suture 2510. Beyond region 2536, deployment suture 2510 passes through further aperture 2538. A further portion 2540 of deployment suture 2510 is disposed in a helical or serpentine configuration. Circumferentially beyond serpentine portion 2540, deployment suture 2510 forms the previously discussed tubular region 2514, including region 2532. Circumferentially beyond region 2532, deployment suture 2510 includes a further portion 2542. Portion 2542 is shown in FIGS. 25 and 27 as being arranged in a substantially linear configuration. The practitioner of ordinary skill in the art will appreciate, however, that the deployment suture is substantially flexible and may assume other arrangements.

Beyond region 2542, deployment suture 2510 reenters aperture 2522 at region 2544 and again traverses passage 2526. After emerging from passage 2526, deployment suture 2510 reenters aperture 2528 at region 2546. Beyond region 2546, deployment suture 2510 again traverses axial cavity 2520, following axial curve 2516 until it reemerges from aperture 2534 at region 2548. Beyond region 2548, deployment suture 2510 re-traverses aperture 2538 and emerges at region 2550.

Referring to FIG. 25, and summarizing the foregoing, deployment suture 2510 proceeds from region 2552 internally within its own axial cavity past region 2532, emerging to form serpentine region 2540, thereafter proceeding externally past region 2532 and thereafter forming linear region 2542 which reenters its own axial cavity to proceed again past region 2532 and to finally reemerge at region 2550. This arrangement allows deployment suture 2510 to constrict into a knot when tension is applied to portions 2550 and 2552. Sliding suture 2512 follows a less convoluted path from a first portion 2560 through region 2546 into axial cavity 2520 (FIG. 26). Traversing axial cavity 2520, sliding suture 2512 emerges from aperture 2534 and passes through aperture 2538 to region 2562. This comparatively direct path allows the position of sliding suture 2512 to be longitudinally adjusted by applying tension to one or the other of regions 2560 and 2562 after the deployment suture 2510 has been tightened to constrict its looped portions into a knot.

Referring again to FIG. 25, region 2532 of deployment suture 2510 has an outer surface region 2570 disposed adjacent to a surface region of stopper portion 2502. In certain embodiments, the surface region of stopper portion 2502 is an external surface region. In other embodiments the surface region of stopper portion 2502 is an internal surface region defining, for example, a through-hole or bore (in contrast to a blind hole). In various embodiments, outer surface region 2570 is substantially fixedly coupled to stopper portion 2502. In other embodiments, outer surface region 2570 is slidingly coupled to stopper portion 2502. In still further embodiments, outer surface region 2570 is disposed in proximity to stopper portion 2502.

Figure 28:
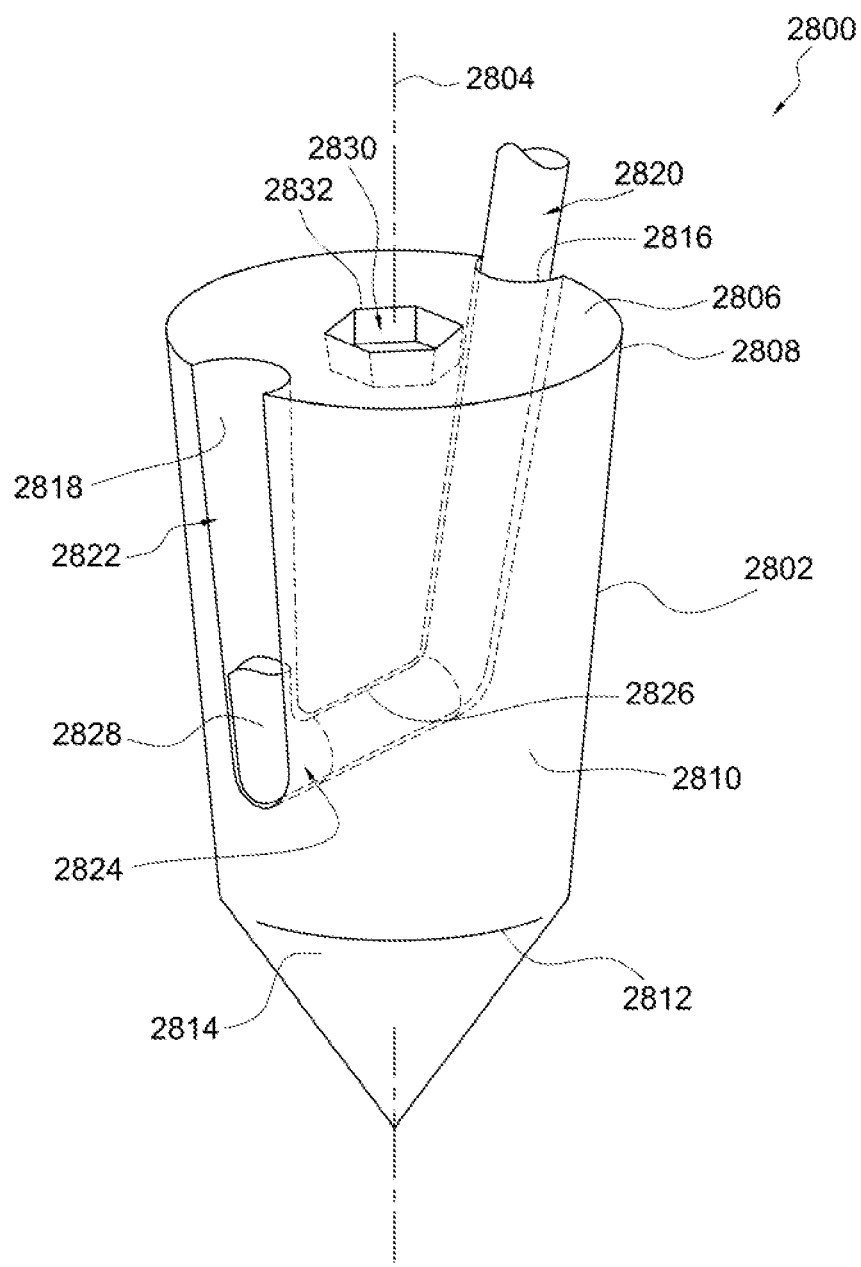
FIG. 28 shows, in schematic view, a further detailed aspects of a stopper portion of an anchor prepared according to principles of the invention.

FIG. 28 shows, in perspective view, a stopper portion 2800 configured according to one embodiment of the invention. The stopper portion includes an elongate body 2802 with a longitudinal axis 2804. The elongate body 2802 includes a generally planar upper surface 2806 with a generally circular circumferential edge 2808. Circumferential edge 2808 adjoins upper surface 2806 and a further circumferential surface 2810. Circumferential surface 2810 is further bounded by a generally circular interface 2812 with a further generally conical surface 2814. Between circumferential edge 2808 and generally circular interface 2814, circumferential surface 2810 tapers towards longitudinal axis 2804. It should be noted that, in certain embodiments, conical surface 2814 will be a blunt or otherwise truncated conical surface. In certain applications, a more pointed conical surface 2814 will allow for a self-puncturing stopper portion that can be inserted without the need for a pre-drilled hole.

In the illustrated embodiment, first 2816 and second 2818 arcuate surface regions define respective first 2820 and second 2822 grooves in circumferential surface 2810. One of skill and the art will appreciate that while the illustrated arcuate surface regions 2816 and 2818 are shown as substantially smooth curves, other configurations, including piecewise planar curves will also be used in respective embodiments. According to the illustrated embodiment, the grooves 2820 and 2822 are disposed in diametrically opposite regions of the circumferential surface 2810, and with respective longitudinal axes generally coplanar with longitudinal axis 2804. A transverse through-hole 2824, or bore, is defined by an internal surface 2826 to provide a continuous opening between 2820 and groove 2822.

As illustrated, the transverse through-hole has a generally circular cross-section, although other configurations including polygonal, elliptical, etc., are also anticipated in various embodiments. It will be readily apparent that the grooves 2820 and 2822, along with the transverse through-hole 2824 are suited to receive and accommodate a suture (or suture assembly) 2828. As noted above with respect to FIG. 25 through-hole 2824 will, in various embodiments, be fixedly coupled to an outer surface of the suture assembly 2820 and in other embodiments, the slidingly coupled to the outer surface of the suture assembly.

In certain embodiments, the surface 2806 will include a recess 2830 arranged to receive a corresponding portion of an insertion tool so as to facilitate insertion of the stopper portion into a prepared recess in a target bone. Typically, the recess 2830 will be generally coaxial with longitudinal axis 2804, although other arrangements are anticipated in respective embodiments. The illustrated recess has a peripheral edge 2832 in the form of a hexagon. Other arrangements are possible, according to the needs of a particular application.

Figure 29:
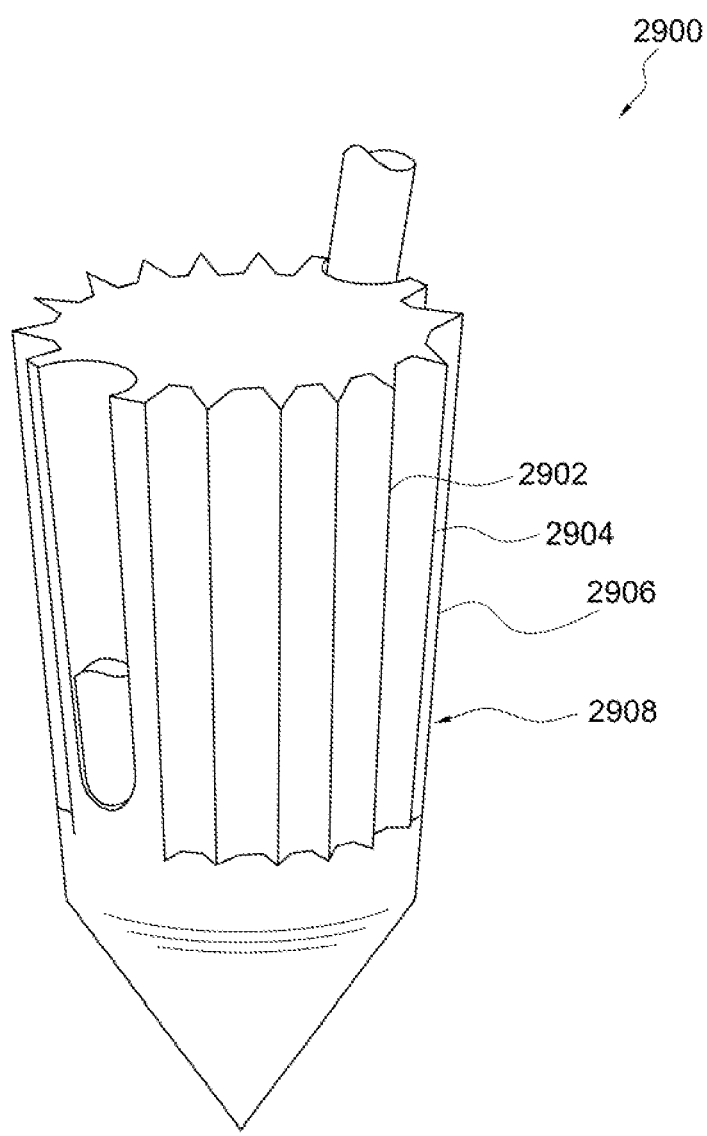
FIG. 29 shows, in schematic view, a further detailed aspects of another stopper portion of an anchor prepared according to principles of the invention.

FIG. 29 illustrates that a variety of other surface configurations of the stopper portion are possible, according to the requirements of particular applications. Thus illustrated stopper portion 2900 includes a plurality of longitudinal striations and protrusions e.g., 2902, 2904, 2906 distributed across a circumferential surface 2908. These exemplary surface features will serve to increase the effective mechanical interaction between the stopper portion and a surrounding bone matrix.

Figure 30:
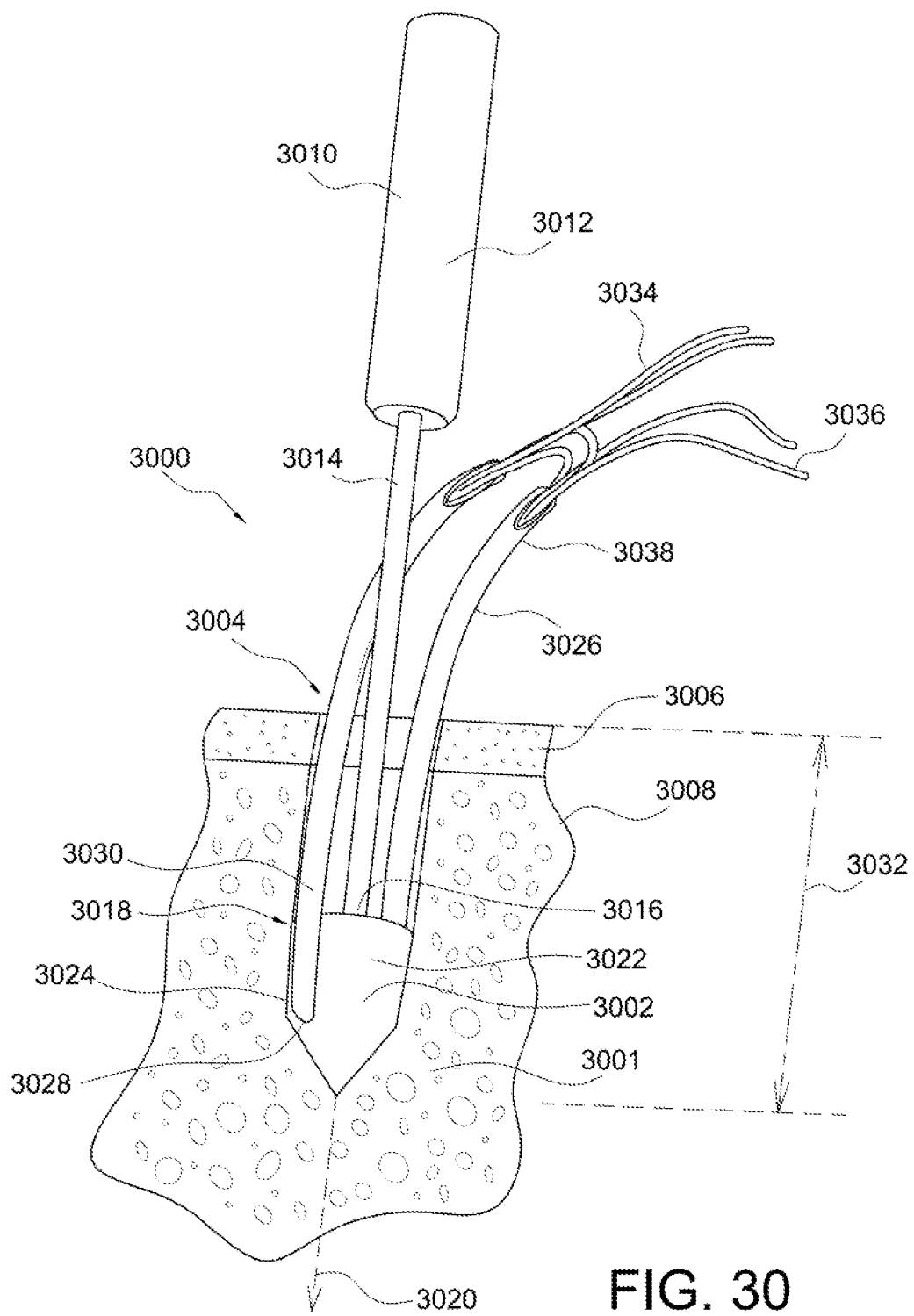
FIG. 30 illustrates certain features of the deployment of an anchor prepared according to principles of the invention.

FIG. 30 shows the exemplary insertion of an anchor 3000 into a bone matrix 3001 according to principles of the invention. As illustrated, a stopper portion 3002 is inserted into a cavity 3004 in the bone matrix. Various procedures may fall within the scope of the invention, including inserting the stopper into a pre-drilled cavity 3004, pressing the stopper into the bone to form the cavity 3004, and predrilling a hole through the cortical bone 3006 and thereafter pressing the stopper portion 3002 into the cancellous bone 3008 to form the balance of the cavity 3004.

In certain embodiments, insertion of the stopper portion 3002 into the bone cavity 3004 is facilitated by the application of an insertion tool, shown as 3010 in the illustrated embodiment. The insertion tool 3010 includes a handle portion 3012 and a shaft portion 3014. A distal end 3016 of the shaft portion 3014 is adapted to interface with an upper end 3018 of the stopper portion 3002 so as to urge the stopper portion into the bone along a direction 3020 that is generally coaxial with the shaft 3014, when a corresponding force is applied to the handle portion 3012.

As illustrated, the stopper portion is inserted through the cortical bone 3006 and into the cancellous bone 3008. The external circumferential surface 3022 of the stopper portion is disposed in close proximity to an internal surface 3024 of the hole. The degree of this proximity will depend in certain instances on whether the hole is pre-formed, or formed by insertion of the stopper portion 3002. In certain applications, an undersized hole having a cross-section less than a corresponding cross-section of the stopper portion will be pre-formed, and the cross-section of the hole will then be expanded by insertion of the stopper portion 3002 into the pre-formed hole. In other embodiments, an undersized hole having a cross-section less than a corresponding cross-section of the stopper portion will be pre-formed. Upon insertion of the stopper portion, a cross-section of the stopper portion will be reduced to match the hole cross-section by a generally elastic compression of the stopper portion. In still further embodiments, a combination of expansion of the bore an elastic compression of the stopper portion will result in a mutual accommodation, such that the stopper portion is fitted snugly within the bore.

In various respective embodiments, pre-forming of the hole will be accomplished by drilling with a twist drill bit, drilling with a speed drill bit, drilling with a Forstner drill bit, drilling with a tubular coring bit, the application of an awl or other sharp device under pressure, laser or other focused-energy, or any other appropriate hole-forming method that is known or becomes known to those of skill in the art.

During insertion of the stopper portion 3002 the fixing portion 3026 is disposed in a relaxed configuration, as shown. Because the fixing portion 3026 is coupled to the stopper portion 3002 at, for example, a through-hole 3028 a leading part 3030 of the fixing portion 3026 is drawn into the hole 3004 after the stopper portion. In certain embodiments, once the stopper portion 3002 has been inserted to a desired depth 3032 within the hole 3004 the shaft portion 3014 of the tool 3010 is withdrawn. Thereafter, tensile forces are applied to the first 3034 and second 3036 ends of deployment suture 3038, drawing the deployment suture, including its various convolutions, into a constricted configuration. In certain alternative embodiments, a preliminary application of tensile forces to the deployment suture 3038 is made prior to withdrawal of the shaft 3014 of the tool 3010. Consequently the tool 3010 tends to maintain the stopper portion 3002 in a substantially fixed location during an initial contraction of the deployment suture. As a result, the stopper portion is not displaced by the tensile forces applied to the deployment suture.

Figure 31:
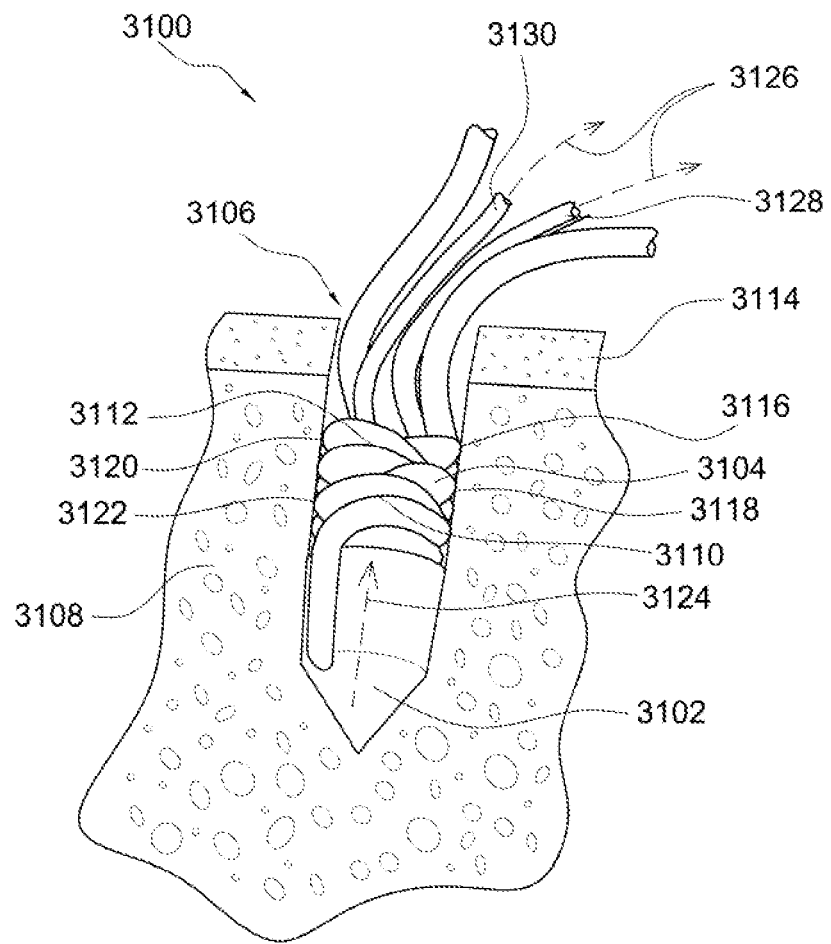
FIG. 31 illustrates still other features of an anchor prepared according to principles of the invention.

FIG. 31 shows an anchor 3100, like anchor 3000 of FIG. 30, in an installed state. The anchor 3100 includes a stopper portion 3102 and a fixing portion 3104. The stopper portion 3102 is disposed within a hole 3106 or cavity in a cancellous bone region 3108. Also within hole 3106 is a fixing portion 3110 of the anchor 3100, including a deployment suture 3112 disposed in a constricted configuration. In effect, in the illustrated embodiment, deployment suture 3112 is formed into a knot in FIG. 31, the constricted deployment suture is substantially disposed within cancellous bone region 3108 and below the cortical bone region 3114.

It will be apparent to one of ordinary skill in art that, in its constricted (or knotted) configuration, the deployment suture forms a wadding within the hole 3106 that serves to substantially fix the portion 3102 within the hole. In its knotted configuration, the deployment suture urges its outwardly facing surface regions e.g., 3116, 3118, 3120, 3122 outward against adjacent surface regions of cancellous bone within the hole 3106. This outward pressure establishes and maintains frictional forces between the outwardly facing surface regions of the deployment suture and the inwardly facing surfaces of the cancellous bone. Because of these frictional forces, the deployment suture tends to oppose a tendency of the stopper portion 3102 to be drawn upward 3124 out of the hole 3106 when tensile forces 3126 are applied to first 3128 and second 3130 portions of a sliding suture.

In various embodiments of the invention, the materials of the deployment suture will be selected to have an elastic characteristic ire compression such that the knot tends to maintain the outward pressure, described above, of surface regions 3116, 3118, 3120 and 3122. Consequently, the knot will tend to expand somewhat over time to maintain frictional contact with the internal surfaces of the cortical bone, even as the cortical bone recedes under the ongoing pressure of the wadding.

Figure 32:
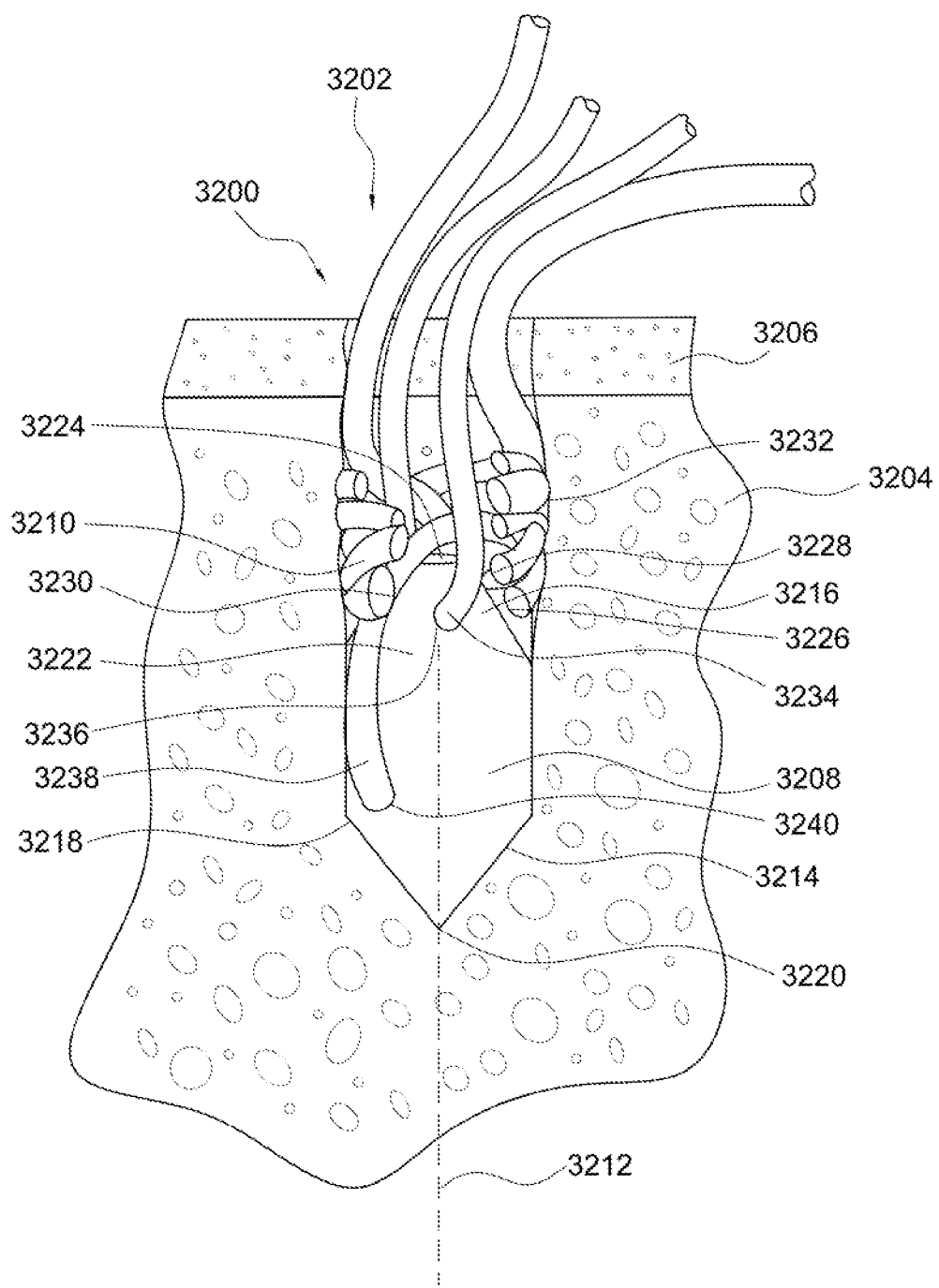
FIG. 32 illustrates still further features of an anchor prepared according to principles of the invention.

FIG. 32 shows, in cutaway perspective view, a further aspect of a suture anchor 3200 according to principles of the invention. The suture anchor 3200 is shown deployed within a hole 3202 in bone tissue. In particular, the suture anchor 3200 is deployed within a region of cancellous bone 3204 and generally below a layer of cortical bone 3206. The anchor 3200 includes a stopper portion 3208 and a fixing portion 3210. The fixing portion 3210 in the illustrated embodiment includes a knotted deployment suture, as described above. As previously noted, however, other configurations of constricted wadding-style fixing portions are also contemplated.

The illustrated stopper portion 3208 includes an elongate body member with a longitudinal axis 3212. In the illustrated embodiment, the body member exhibits a generally circular axial symmetry about the longitudinal axis 3212. The body member tapers towards longitudinal axis 3212 both in a distal region 3214 and in a proximal region 3216. In the illustrated embodiment, the distal taper is shown to exhibit a generally parabaloid surface region 3218 concluding at a substantially pointed distal end 3220. It should be understood, however, that other configurations including, for example, a generally conical surface region, or a generally pyramidal surface region, are also contemplated.

As illustrated, the tapered proximal region also includes parabaloid region 3222 ending at a recess 3224. The recess 3224 is adapted to receive an end of an insertion tool as described above in relation to tool 3010 of FIG. 30. The taper of proximal region 3216 is arranged and configured to serve as a wedge that applies outward radial forces against respective inner surface regions, e.g., 3226, 3228, 3230 of the constricted deployment suture or wadding that constitutes the fixing portion 3210. The outward radial forces include forces perpendicular to longitudinal axis 3212 and serve to urge the wadding material radially outward against the surface regions of cancellous bone, e.g., 3232 that define the hole 3202. As a consequence of this outward urging, frictional forces between outward facing surface regions of the wadding material, and the corresponding inward facing surface regions of the cortical bone are increased. The result is an improved ability of the fixing portion to retain its position within the hole 3202 and to maintain the stopper portion desirably at its installed location.

In a further aspect, according to principles of the invention, a portion of a sliding suture 3234 is disposed within a separate through-hole 3236 defined relatively close to the proximal end of the stopper portion. The separate through-hole 3236 defined in axis disposed generally transverse to longitudinal axis 3212, being in some embodiments perpendicular to longitudinal axis 3212 and in others disposed at an oblique angle with respect to longitudinal axis 3212. In the illustrated embodiment, a portion of the deployment suture 3238 is disposed in a transverse through-hole 3240 defined relatively close to the distal end of the stopper portion and similar to through-hole 2824 described above in relation to FIG. 28. It should be understood, however, that other arrangements are possible, including arrangements in which both the deployment suture and the sliding suture traverse distal through-hole 3240.

One of skill in the art will appreciate that, where desirable, disposing the sliding suture through a separate and appropriately configured through-hole will facilitate the sliding of the sliding suture subsequent to adjusting the deployment suture into its constricted configuration. In addition, coupling the sliding suture directly to the stopper portion will improve the transmission of tensile forces applied by the sliding suture to the stopper portion, rather than to a distal end of the constricted deployment suture wadding. As a result, the proximal region 3216 of the stopper, portion will be more effective in applying outward radial forces to the fixing portion.

Figure 33:
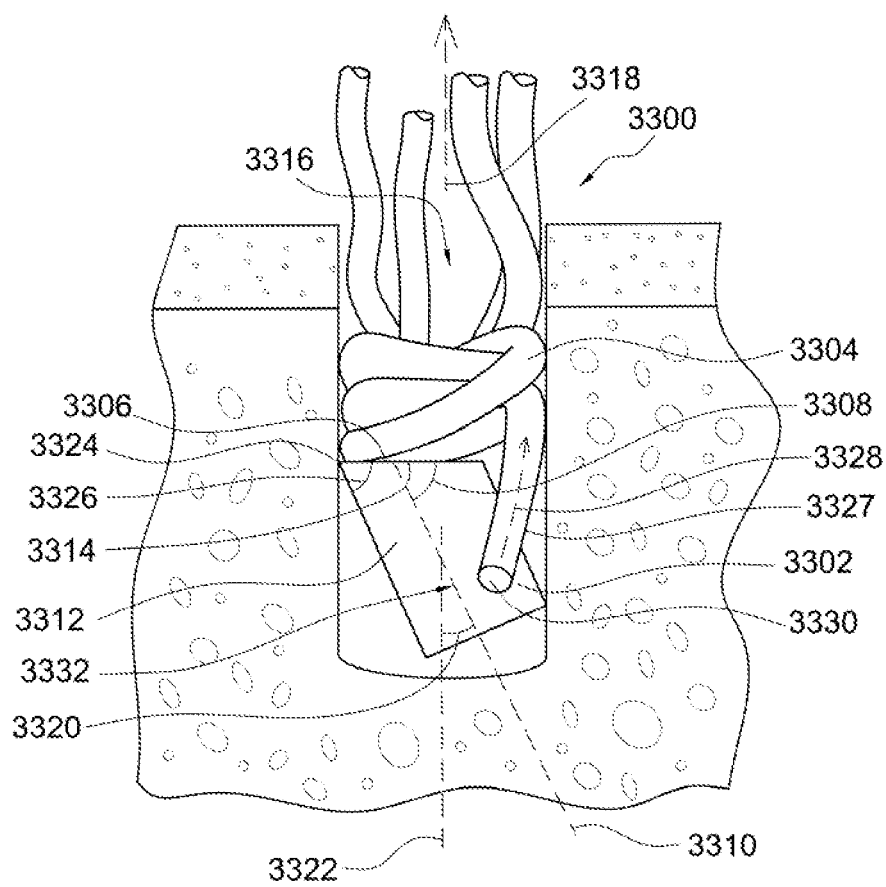
FIG. 33 illustrates still further features of an exemplary anchor prepared according to principles of the invention.

FIG. 33 illustrates further aspects of an anchor 3300 prepared according to principles of the invention. The anchor 3300 includes a stopper portion 3302 and a fixing portion 3304. In the illustrated embodiment, the stopper portion 3302 includes an upper surface 3306 disposed at an oblique angle 3308 with respect to a longitudinal axis 3310 of the stopper portion. Upper surface 3306 meets a circumferential surface 3312 at a circumferential edge 3314.

In certain embodiments, a cross-section of the stopper portion 3302 is chosen to be somewhat smaller than a corresponding cross-section of a hole 3316, in which the anchor is disposed. As a result, the stopper portion can be arranged to cock in response to a force applied in a direction 3318. As it cocks, longitudinal axis 3310 of the stopper portion 3302 forms an angle 3320 with respect to longitudinal axis 3322 of the hole 3316.

Because upper surface 3306 is disposed at oblique angle 3308, circumferential edge 3314 includes a region 3324 where upper surface 3306 forms an acute angle 3326 with circumferential surface 3312. Consequently, as the stopper cocks, region 3324 of edge 3314 tends to interfere with, and become embedded into, an adjacent region of bone. Region 3324 thus serves as a barb that is effective to hold stopper portion 3302 in place within hole 3316 against forces applied along direction 3318.

It will be evident to one of skill the art that tension applied to a deployment suture 3327 along axis 3328 will tend to effect and reinforce the cocking of the stopper portion and thus maintain the interference of region 3324 with adjacent bone. Moreover, as fixing portion 3304 assumes a constricted or knotted configuration, as shown, the resulting knot also tends to interfere with the surrounding bone, resulting in frictional forces that both directly resist outward displacement of the stopper portion and tend to maintain tension on the deployment suture 3327 along direction 3328, and thus maintain interference between region 3324 and adjacent bone.

It will be apparent that, in the illustrated embodiment, deployment suture 3327 is disposed within and through a bore or through-hole 3330 through the body of stopper portion 3302. In addition, in certain embodiments, through-hole 3330 is displaced or offset with respect to longitudinal axis 3310 by a distance 3332 chosen according to the requirements of a particular application. This displacement serves to further motivate cocking of the stopper portion 3302 within the hole 3316 and thus improve the desirable interference between region 3324 and the adjacent bone.

It will be appreciated that stopper portion 3302 will, in certain embodiments, exhibit a circular symmetry around longitudinal axis 3310, except for the effect of angle 3308. Consequently, the stopper portion 3302 will, for the most part, have a circular cross section. In other embodiments, however, the stopper portion 3302 will have a polygonal cross-section such as, for example and without limitation, a triangular cross-section, a square cross-section, a rectangular cross section, a pentagonal cross-section, a hexagonal cross-section or any other regular polygonal cross-section, as well as irregular polygonal cross-section, curved cross sections of all varieties, stellate cross-sections, etc.

Figure 34:
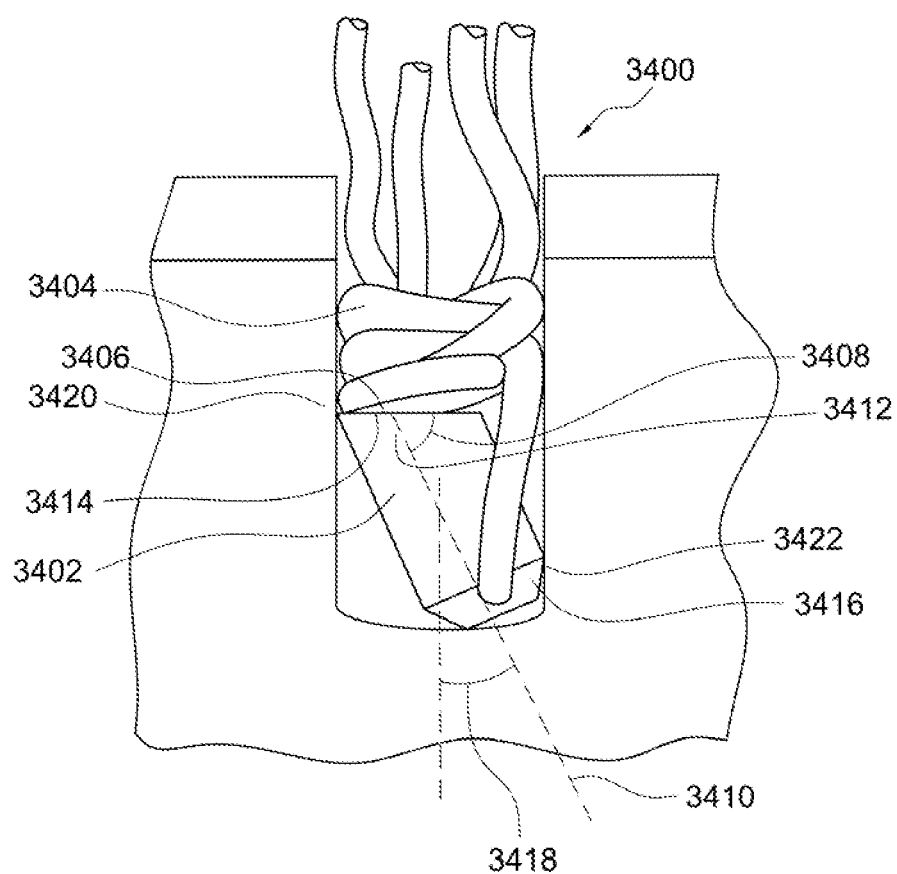
FIG. 34 illustrates additional features of an exemplary anchor prepared according to principles of the invention.

FIG. 34 shows further aspects of an anchor 3400 prepared according to principles of the invention. Like anchor 3300 of FIG. 33, anchor 3400 includes a stopper portion 3402 and a fixing portion 3404. In the illustrated embodiment, the stopper portion 3402 includes an upper surface 3406 disposed at an oblique angle 3408 with respect to a longitudinal axis 3410 of the stopper portion. Upper surface 3405 meets a circumferential surface 3412 at a circumferential edge 3414.

Anchor 3400 includes a circumferential bevel or taper 3416 at its distal end. As is evident on inspection, bevel 3416 allows the stopper portion 3402 to cock fully, such that angle 3418 is maximized. This maximization tends to improve a desirable interference between the stopper portion 3402, and an adjacent region of bone 3420. While, as illustrated, the bevel is configured as having a conical form, one of skill in the art will appreciate that other configurations, including curved configurations will also be desirable in some applications. In particular, bevel 3416 may include, in some embodiments, pointed and/or hooked protrusions (not shown) adapted to interfere effectively with the bone in region 3422.

Figure 35:
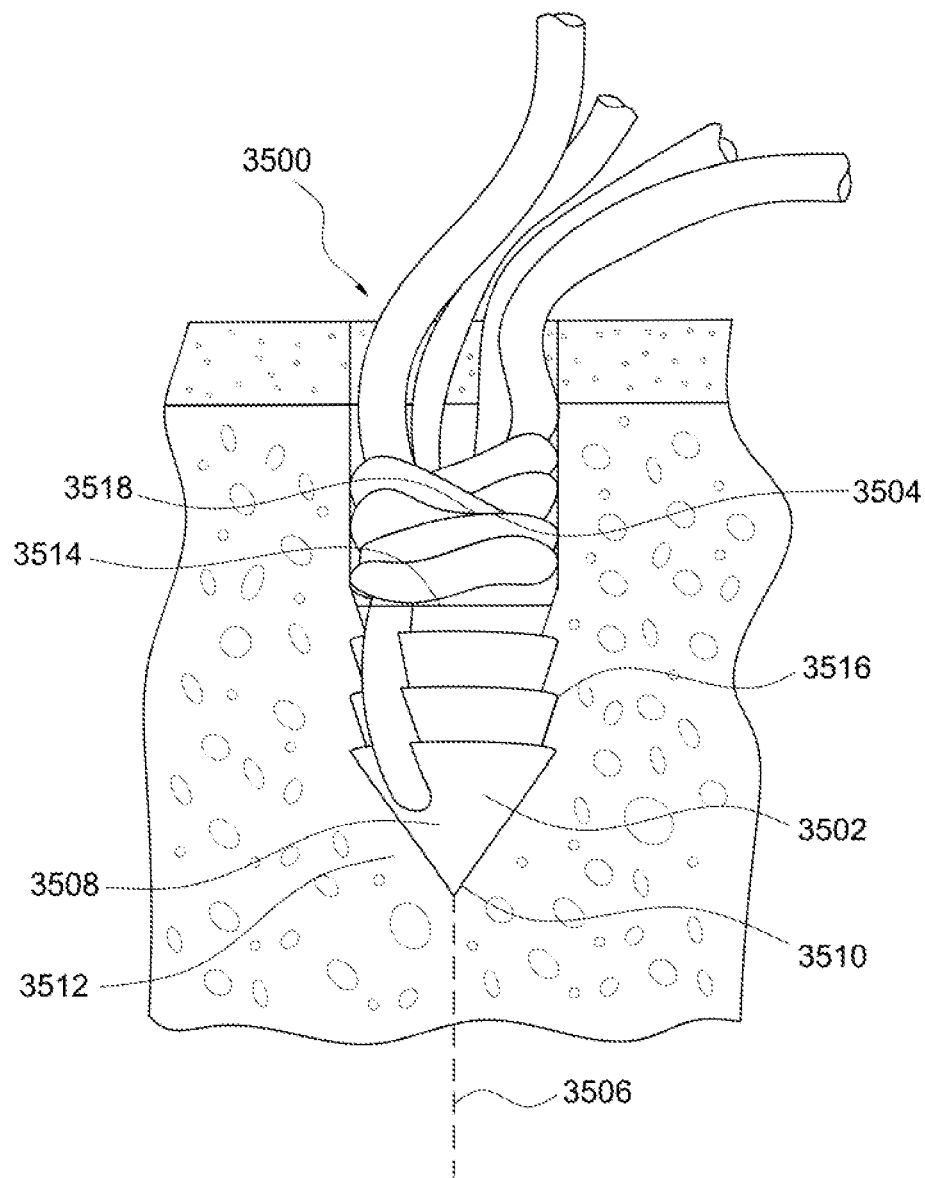
FIG. 35 illustrates other aspects of an anchor prepared according to principles of the invention.

FIG. 35 shows further aspects of an anchor 3500 according to principles of the invention. The anchor 3500 includes a stopper portion 3502 and a fixing portion 3504. As illustrated, stopper portion 3500 includes a body member having a generally cylindrical circular symmetry about a longitudinal axis 3506. A distal end 3508 of stopper portion 3502 tapers to a point 3510 across a conical or curved surface region. In certain aspects, the invention includes a method of inserting the stopper portion 3502 into a target bone region 3512 by applying pressure to a proximal end 3514 of the stopper portion. One or more circumferential barbs e.g., 3416 are arranged to interfere with surrounding bone so as to resist withdrawal of the stopper portion 3502 from its inserted location within the bone. As also shown, fixing portion 3504, in the illustrated constricted configuration, forms a wadding with external surface regions 3518 that also interfere with surrounding bone to resist withdrawal of the stopper portion 3502.

Figure 36:
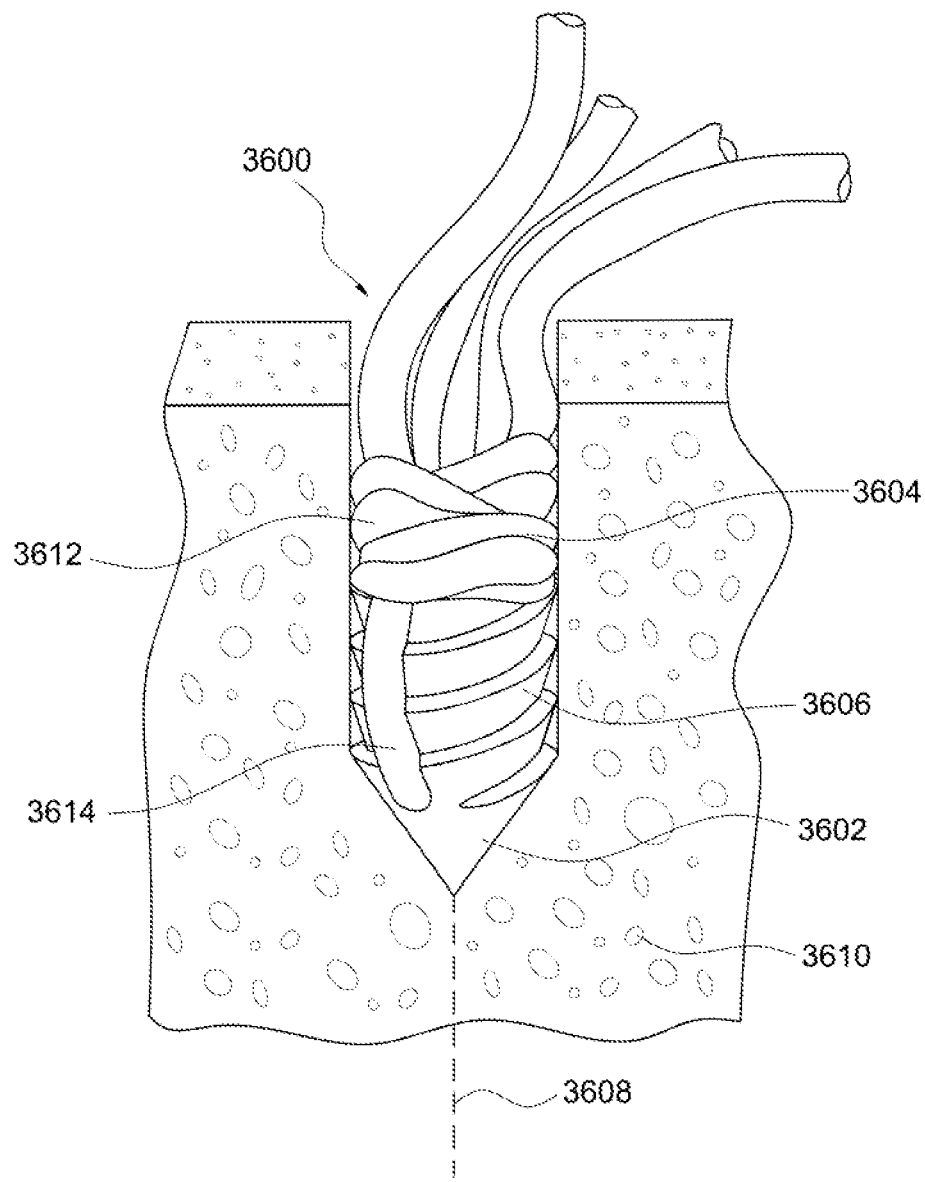
FIG. 36 illustrates still further features of an anchor prepared according to principles of the invention.

FIG. 36 shows an anchor 3600 that is similar in most respects to anchor 3500 and includes both a stopper portion 3602 and a fixing portion 3604. In place of circumferential barbs 3516, however, stopper portion 3602 includes one or more helical threads 3606. It will be readily understood that a properly oriented rotation of stopper portion 3602, about its longitudinal axis 3608 during insertion, will tend to draw the stopper portion into the surrounding bone 3610 due to interference of the threads 3606 and the bone. This interference will improve retention of the stopper portion within the bone, as compared with a stopper portion having a smooth, unthreaded surface.

After insertion of the stopper portion 3602 into the bone, the fixing portion 3604 is drawn into its constricted configuration. Interference between external surface regions 3612 of the fixing portion 3604 and surrounding bone serves to oppose rotation of the constricted fixing portion within the bone (i.e., about axis 3608). Because the constricted fixing portion 3604 is coupled to stopper portion 3602 by deployment suture 3814, the opposition of the fixing portion 3604 to rotation is transferred to the stopper portion 3602. By thus preventing rotation of the stopper portion 3602, the fixing portion 3604 acts in conjunction with the threads 3606 to oppose withdrawal of the stopper portion 3602 from the surrounding bone.

Figure 37:
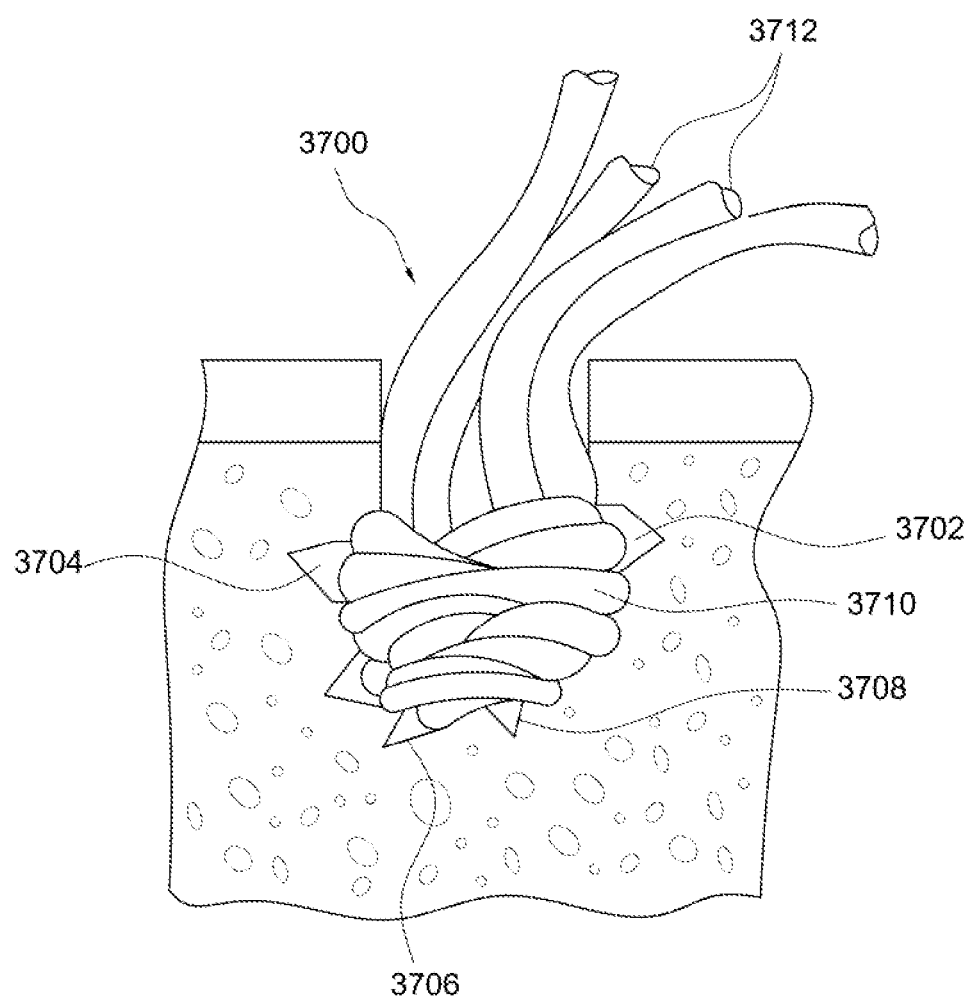
FIG. 37 illustrates still other features of an anchor prepared according to principles of the invention.

FIG. 37 shows an anchor 3700 according to principles of the invention including a plurality of stopper portions, e.g., 3702, 3704, 3706, 3708, and a fixing portion 3710. In various embodiments, the stopper portions are coupled to the fixing portion 3710 by disposing a portion of the fixing portion within a respective through-hole of the individual stopper portion. In exemplary embodiments, one or more of the stopper portions will be configured to include pointed, sharpened or barbed features, or other features adapted to promote a coupling interference of the stopper portion with surrounding bone when the fixing portion 3710 is drawn into the illustrated constricted configuration. It will be understood, that as the fixing portion constricts, it tends to expand laterally towards the surrounding walls of a hole in which it is disposed. This lateral expansion drives the stopper portions against and/or into the surrounding bone where the combined effect of the stopper portion and fixing portion tends to anchor a sliding suture 3712 to the bone.

Figure 38:
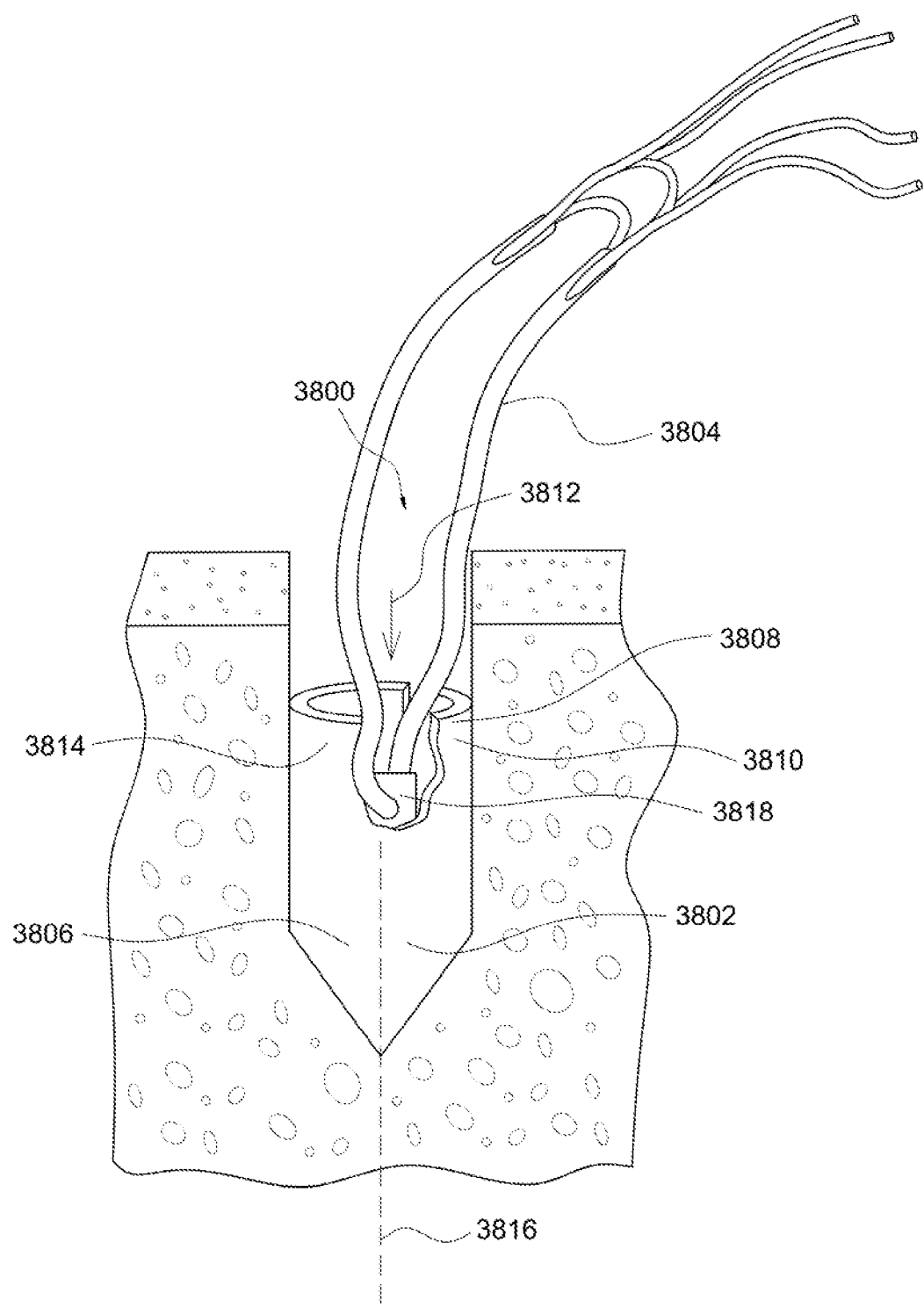
FIG. 38 illustrates still other features of an anchor prepared according to principles of the invention.

FIG. 38 shows, in cutaway perspective view, an anchor 3800 prepared according to principles of the invention. Consistent with previously described embodiments, anchor 3800 includes a stopper portion 3802 and a fixing portion 3804. Fixing portion 3804 includes a flexible material and is arranged and configured to transition from an un-constricted configuration (as shown) to a constricted or knotted configuration, in which constricted configuration the fixing portion serves as a wadding.

In the illustrated embodiment, the stopper portion 3802 includes a first generally solid distal region 3806 and a plurality of flanges e.g., 3808. Each flange includes an external surface region 3810 and an internal surface region disposed inwardly of, and in radially spaced relation to, the external surface region 3810. The internal surface regions of the flanges define a recess or cavity 3812 at a distal end 3814 of the stopper portion 3802.

The material of the flanges is chosen, and the structure of the flanges is prepared, so that the flanges exhibit a desirable flexibility. In certain embodiments, this flexibility will include a substantially elastic characteristic. In other embodiments, this flexibility wilt include a relatively inelastic, substantially malleable characteristic. In certain embodiments, the flexibility of the flanges will be anisotropic, so that the flanges tend primarily to deform radially outward, away from a longitudinal axis 3816, rather than in other directions. In certain embodiments, various combinations of elasticity, malleability, and isotropy will be found in, between and among individual flanges.

As shown, the stopper portion 3802 includes a coupling feature 3818 configured for coupling the fixing portion 3804 to the stopper portion 3802. In the illustrated embodiment, the coupling feature includes a generally rectangular tab having a through-hole, where a part of the fixing portion 3804 is disposed within and through the through-hole. One of skill in the art will appreciate, however, that a wide variety of other coupling features will be found in various embodiments, according to the requirements of a particular application. In addition, it will be apparent that the coupling feature, or other region, of the stopper portion, will include, in certain embodiments, a recess or other feature appropriate to interface with an insertion tool.

Figure 39:
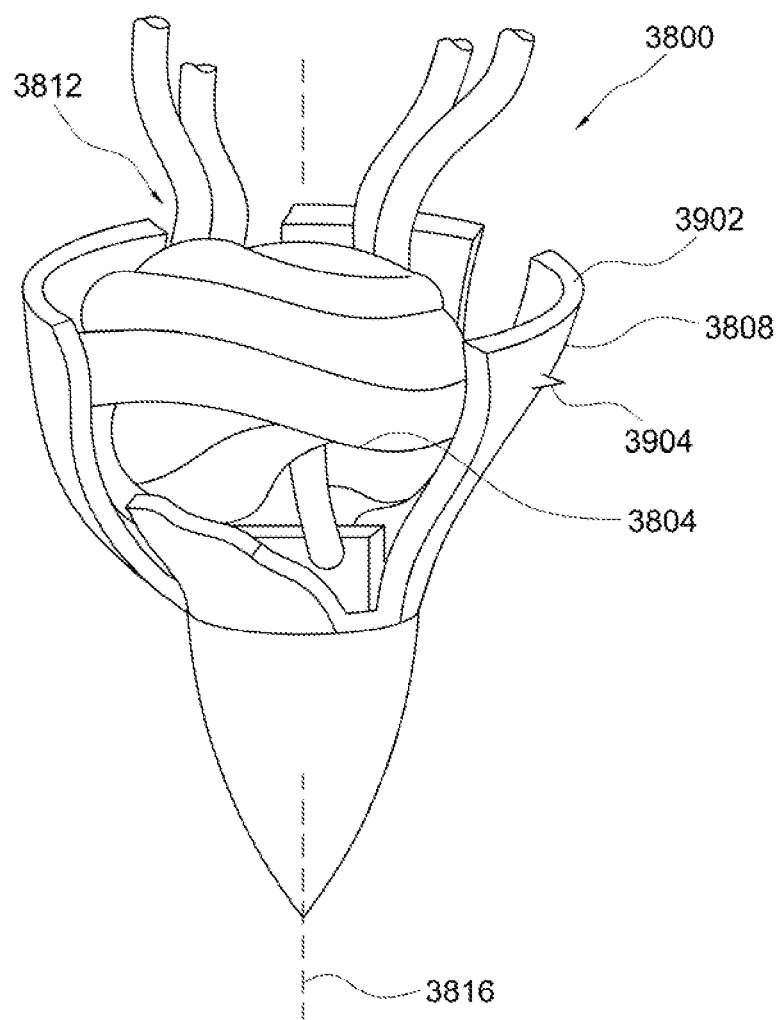
FIG. 39 provides further information regarding an anchor prepared according to principles of the invention.

FIG. 39 shows the anchor 3800 of FIG. 38 in a deployed configuration. The fixing portion 3804 is shown in a constricted or knotted configuration that forms a wadding within the recess 3812. It will be apparent, that the lateral expansion of the wadding, resulting from constriction of the fixing portion tends to urge the flanges e.g., 3808 outwardly and away from longitudinal axis 3816. As the flanges are urged outwardly, they tend to interfere mechanically with, and consequently couple to surrounding one (or any other surrounding media). This coupling serves to retain the anchor 3800 in a desired installed location, consistent with principles of the invention. One of skill in the art will appreciate that the flanges e.g., 3808 will include, in respective embodiments, a variety of desirable features, as described above or known in the art, tending to improve interaction of the flange with the surrounding medium. Thus, for example, the flange may include a sharp external circumferential edge 3902, and/or a radial protrusion 3904 and/or any other appropriate feature.

As previously noted, certain embodiments of the fixing portion will include a substantially elastic material such that a wadding in the constricted configuration will tend to maintain an elastic outward pressure that beneficially improves retention of the stopper portion. Such elastic material may be included in a structural portion of the fixing portion, and/or may include a coating or other layer applied or otherwise disposed externally to the fixing portion during manufacturing. Thus, in certain embodiments, the fixing portion may include an elastomeric material having favorable characteristics including desirable biocompatibility, elasticity, and/or adherent and frictional characteristics.

Further, it should be understood that while FIG. 39 illustrates one constrictible fixing portion, a wide variety of arrangements and configurations are consistent with the broad invention. Thus, a fixturing portion according to principles of the invention will include features selected and formed to impede or prevent the withdrawal of a stopper portion from a desirable installed location.

FIGS. 40A and 40B shows a further exemplary fixturing portion 4000 in a relaxed configuration and a constricted configuration respectively. The fixturing portion 4000 includes, for example, a webbing portion 4002 and a deployment suture, 4004. It is to be understood that sliding sutures will also be included in certain embodiments, but are omitted here and below for clarity. Webbing portion 4002 will, in various embodiment, include one or more of a textile material such as a woven textile material, a felted textile material or other textile material, a polymer material, such as a polymer yarn, an extruded polymer, a polymer ribbon, an elastomeric polymer material, and a metallic material including, for example, a substantially biocompatible substantially elastomeric metallic material. In certain embodiments, the fixturing portion will include a plurality of apertures, e.g., 4012, 4014, 4016, within which an insertion tool may be temporarily disposed. After installation of the anchor, such a tool will be withdrawn.

It will be apparent upon inspection, and in light of the foregoing discussion, that the application of tensile forces to the deployment suture 4004 will constrict the webbing portion 4002. Consequently, dimension 4006 will tend to expand as the webbing portion transitions from the un-constricted to the constricted configuration. As a result, surface regions e.g., 4008, 4010 will be urged radially outwardly 4012, the better to interfere with a surrounding matrix of bone or other media.

Figure 40C:
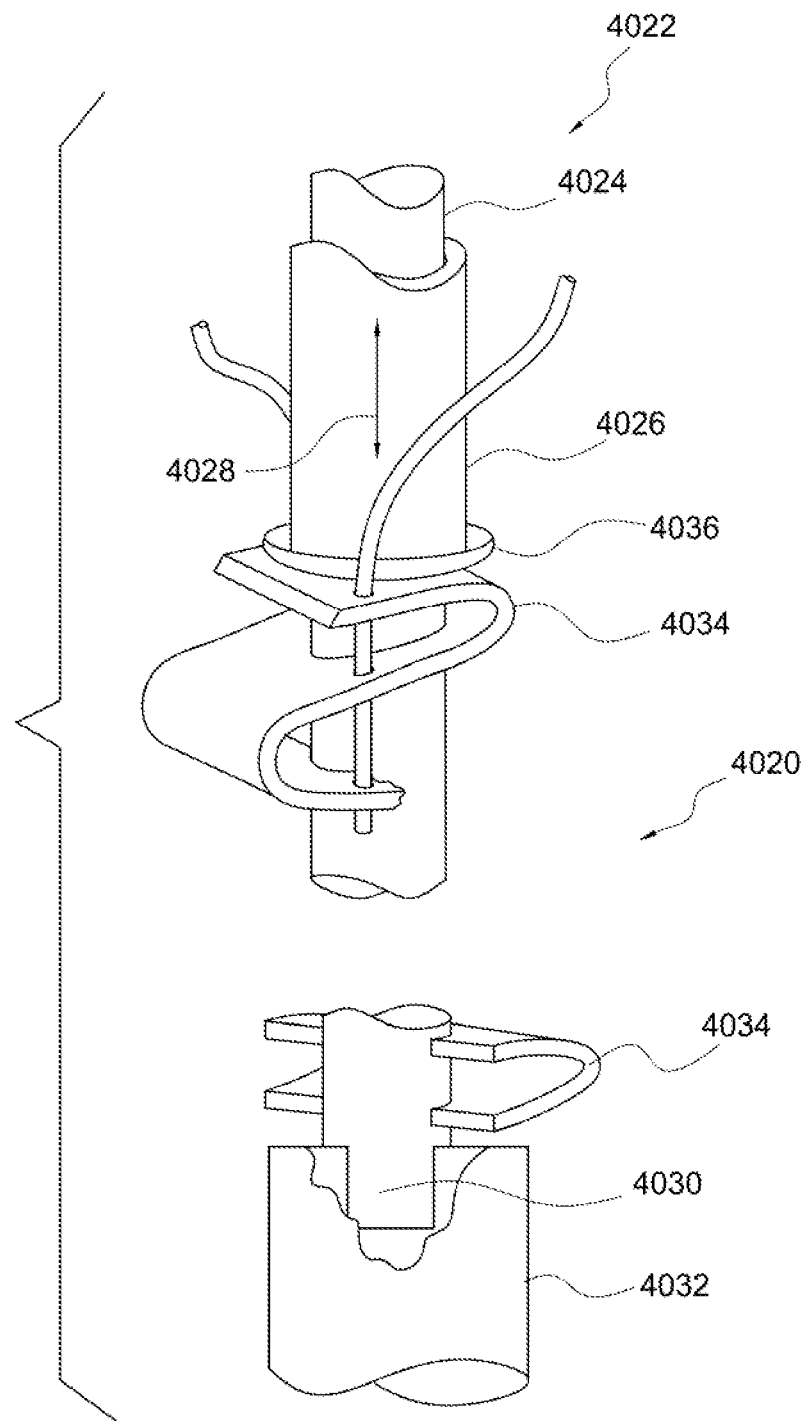
FIG. 40C illustrate still further features of an anchor prepared according to principles of the invention including features related to deployment of the same.

In an alternative embodiment, as shown in FIG. 40C, a suture anchor 4020 according to principles of the invention is arranged to receive an installation tool 4022 having an installation shaft 4024. In certain embodiments, the installation shaft will be mounted to a handle (not shown) for ease of manipulation. A tamper portion 4026 is slidingly coupled to the shaft 4024. The tamper portion 4026 is arranged to slide along a direction 4028. In the illustrated embodiment, the tamper portion is shown as a cannulated member having an axial bore within which the shaft 4024 is disposed. It will be understood, however, that other mobile arrangements of the tamper portion are also contemplated to be within the scope of the present disclosure.

As shown in cutaway view, a distal end 4030 of the shaft 4024 is arranged to be coupled to a rigid portion 4032 of the suture anchor 4020. In the illustrated embodiment, the distal end 4030 is received within a corresponding aperture of the rigid portion 4032. A similar coupling, with or without a tamper, would, for example, be applicable in relation to anchor 3400 of FIG. 34. It will again be appreciated that other arrangements for temporarily coupling the shaft 4024 to the rigid portion 4032 are contemplated. The illustrated tamper shows a distal end formed into a smooth pushing surface 4036, but other arrangement are also contemplated.

In light of the present disclosure, taken in its entirety, one of skill in the art will appreciate that a motion of the tamper portion 4026 can readily be achieved which results in a transition of the webbing portion 4034 (or other wadding device) from an un-constricted to a constricted state. Also in light of the present disclosure, it will be apparent that such a motion can be activated by a manual action of the user, or by other arrangements and apparatus including, for example, a spring, a magnet, device, an active or passive actuator of any known description, etc. In particular, an actuation mechanism can be provided that allows for one-handed installation and activation of the suture anchor.

Figures 40D, 40E:
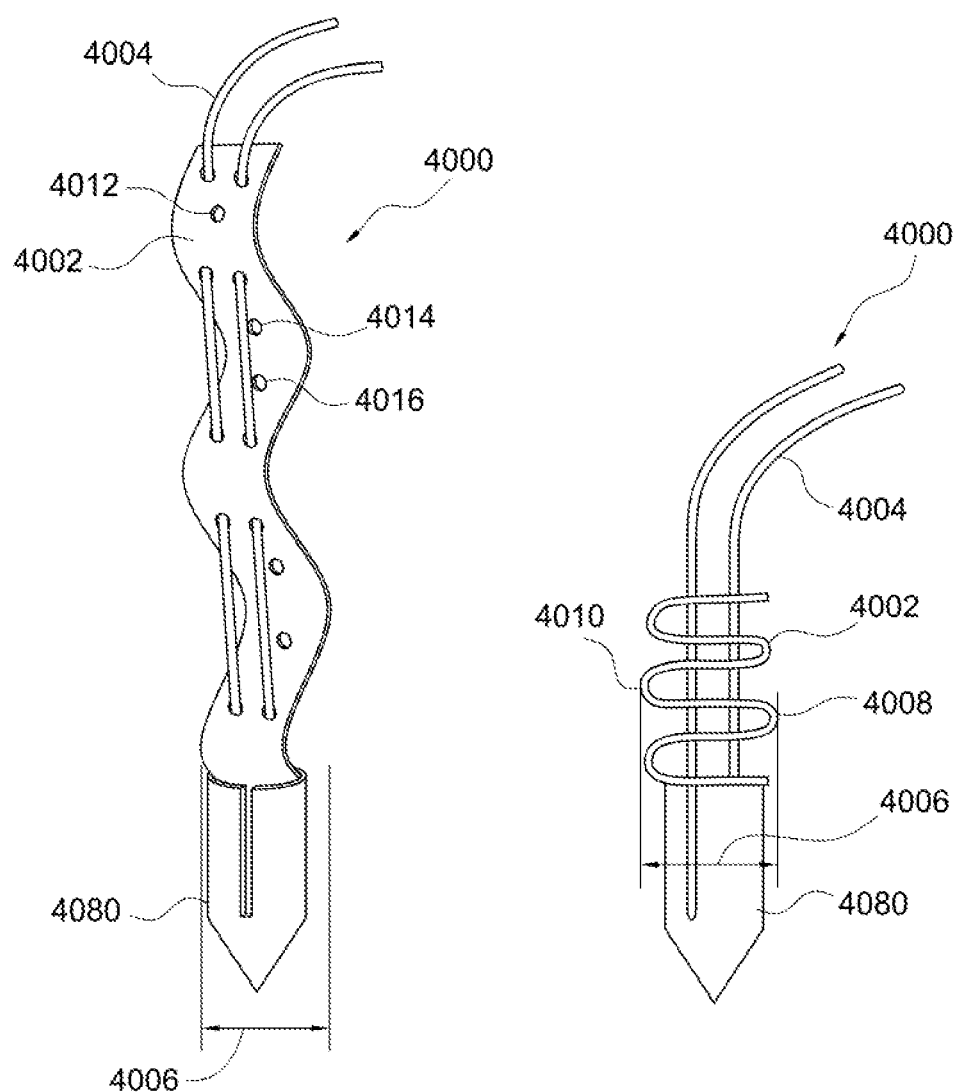
FIGS. 40D-40E illustrate additional arrangements of an anchor prepared according to principles of the invention including features related to deployment of the same.

FIGS. 40D and 40E show an exemplary fixturing portion 4000 coupled to a corresponding stopper portion 4080 and disposed in an un-constricted and constricted configuration respectively.

Figure 41B:
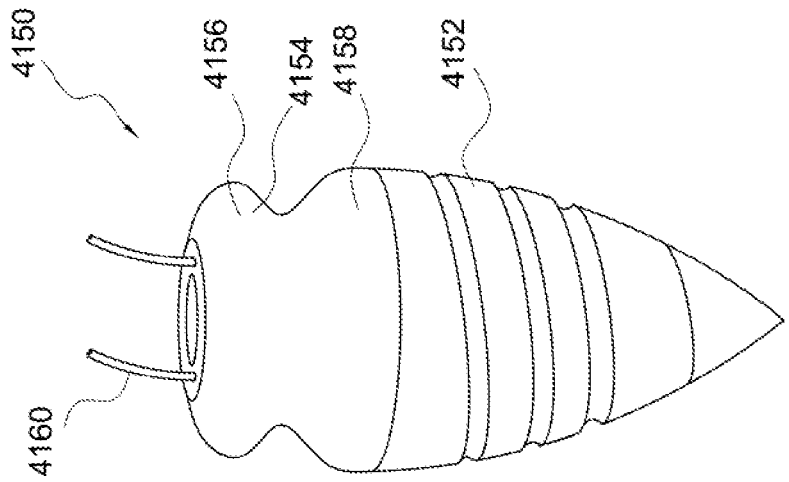
FIGS. 41A-41B illustrate still further features of an anchor prepared according to principles of the invention.
Figure 41A:
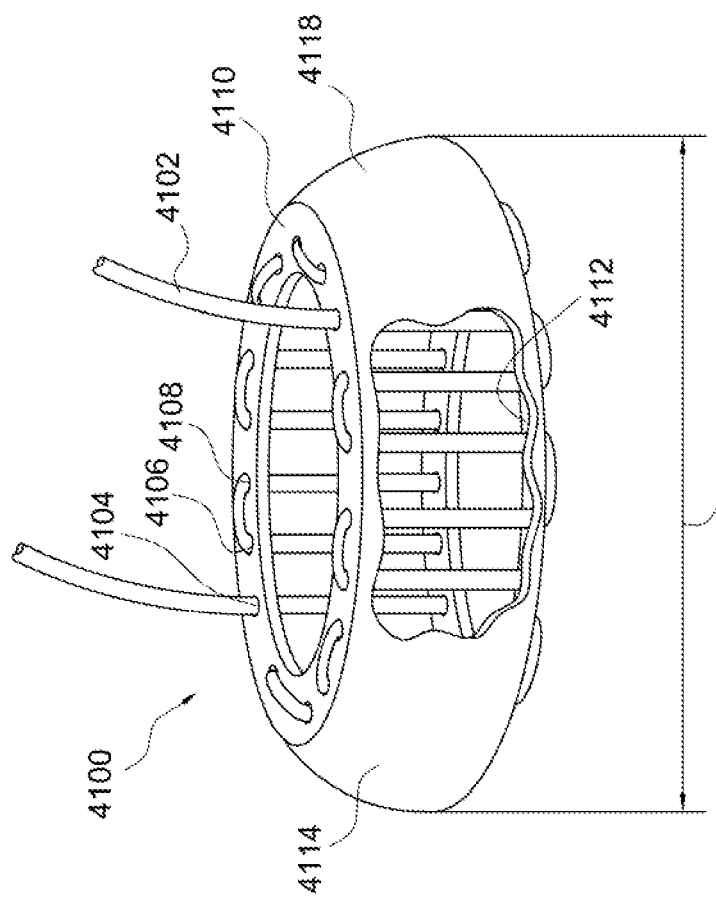

FIG. 41A shows still another fixing portion 4100 prepared according to principles of the invention. As is apparent upon inspection, a deployment suture 4102 is disposed in serpentine fashion through a plurality of holes e.g., 4104, 4106, 4108 in upper 4110 and lower 4112 circumferential flanges of the fixing portion 4100. When tensile forces are applied to the protruding portions of the deployment suture 4102, the upper 4110 and lower 4112 circumferential flanges are drawn axially towards one another. A circumferential portion 4114, disposed between the upper and lower flanges, is arranged to expand radially so as to enlarge dimension 4116 as the flanges move towards one another. Consequently, an outer surface region 4118 of circumferential portion 4114 is urged towards a surrounding matrix of bone or other media, where it interferes mechanically to secure a stopper portion (not shown) in a desired location. One of skill in the art will readily appreciate that fixing portion 4100 will include, in various embodiment, any of a wide variety of appropriate materials including for example, and without limitation, polymer materials and metallic materials.

It should be noted that, in certain embodiments, a sliding suture will be disposed coaxially within the deployment suture 4102. In other embodiments, a sliding suture will be separately coupled to a stopper portion disposed inwardly on the fixing portion. In any event, the deployment suture will, in certain embodiments, serve to couple the fixing portion to the stopper portion by, for example, passing a portion of the deployment suture through a bore or through-hole of the stopper portion in the course of its serpentine path.

FIG. 41B shows a further anchor 4150 prepared according to principles of the invention. Anchor 4150 includes a stopper portion 4152 and a fixing portion 4154. Fixing portion 4154 is arranged to operate on the general principles of fixing portion 4100, however it will be apparent that fixing portion 4154 includes two bellows portions 4156 and 4158 whereas fixing portion 4100 will be understood to include a single bellows. One of skill in the art will understand that any appropriate number of bellows will be employed in a particular application of the invention.

It should be further noted that the surface features of stopper portion 4152 are exemplary only, and that any of the previously described or suggested surface features, or any other feature appropriate to a particular embodiment of the invention, will be equally well within the scope of the invention. Furthermore, it should be noted that stopper portion 4152 and fixing portion 4154 will, in various embodiments, be coupled to one another by a portion of deployment suture 4160, or by any other appropriate means, and that in certain embodiments, stopper portion 4152 and fixing portion 4154 will be integrally formed and/or substantially fixedly coupled to one another.

More generally, it should be understood that the particular configuration of the bellows should not be understood as limiting. For example, an elastomeric envelope enclosing a gas, liquid, gel or particulate medium will also provide the requisite lateral expansion. Moreover, such an expansion can be used, and is disclosed for the purposes of, effecting an interlock between two substantially rigid portions of an anchor. Hence, the interlock described above between, for example the stopper portion and fixing portion of anchor 1100 (of FIG. 11) can be further motivated and insured by disposing a device like fixing portion 4100 between detent devices 1106, 1110 1112.

Figure 42A:
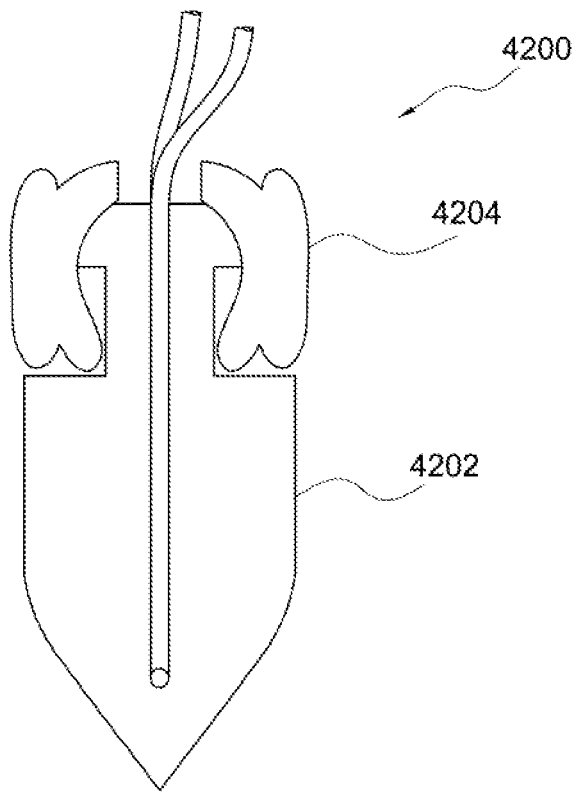
FIGS. 42A-42B illustrate yet further features of an anchor prepared according to principles of the invention.
Figure 42B:
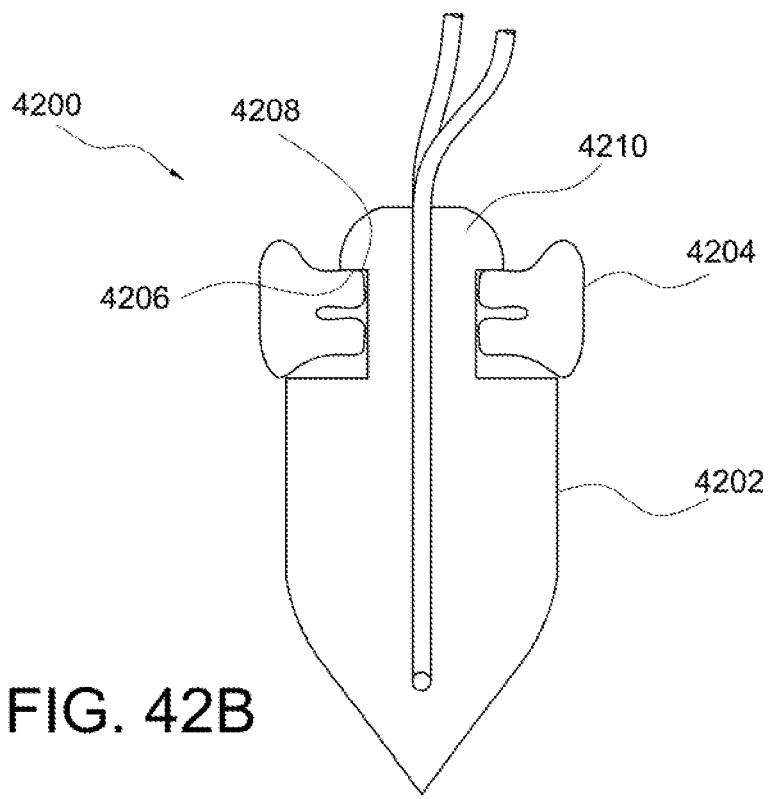

FIGS. 42A and 42B show, in sectional schematic view, a further arrangement of a suture anchor 4200 including a substantially rigid stopper portion 4202 and a flexible and/or elastic wadding portion 4204. FIG. 42A illustrates suture anchor 4200 in a first un-constricted state and FIG. 42B shows the same anchor 4200 in an activated and constricted state. It will be evident upon inspection that the constricted configuration of the wadding portion 4204 is maintained, once activated, by the mechanical interference of a surface region 4206 of the wadding portion 4204 with a corresponding surface region 4208 of a barbed feature 4210 of the substantially rigid portion 4202.

In certain embodiments of the invention, the wadding portion 4204 will include elastomer material. Elastomer materials that may be used in various embodiments of the invention include various copolymers or block copolymers (Kratons®) available from Kraton Polymers such as styrene-butadiene rubber or styrene-isoprene rubber, EPDM (ethylene propylene diene monomer) rubber, nitrile (acrylonitrile butadiene) rubber, polyurethane, polybutadiene, polyisobutylene, neoprene, natural latex rubber and the like. Foam materials may be closed cell foams or open cell foams, and may include, but is not limited to, a polyolefin foam such as a polyethylene foam, a polypropylene foam, and a polybutylene foam; a polystyrene foam; a polyurethane foam; any elastomeric foam made from any elastomeric or rubber material mentioned above; or any biodegradable or biocompostable polyesters such as a polylactic acid resin (comprising L-lactic acid and D-lactic acid) and polyglycolic add (PGA) polyhydroxyvalerate/hydroxybutyrate resin (PHBV) (copolymer of 3-hydroxy butyric acid and 3-hydroxy pentanoic add (3-hydroxy valeric acid) and polyhydroxyalkanoate (PHA) copolymers; and polyester/urethane resin. One of skill in the art will appreciate that the foregoing are exemplary of a wide variety of possibilities that would be applied in an appropriate applications and are not intended as limiting in any way.

One of skill in the art will appreciate that an appropriately configured installation tool, including a tamper portion as suggested by FIG. 40C, will be beneficially employed in the installation of a suture anchor such as anchor 4200.

Figure 43A:
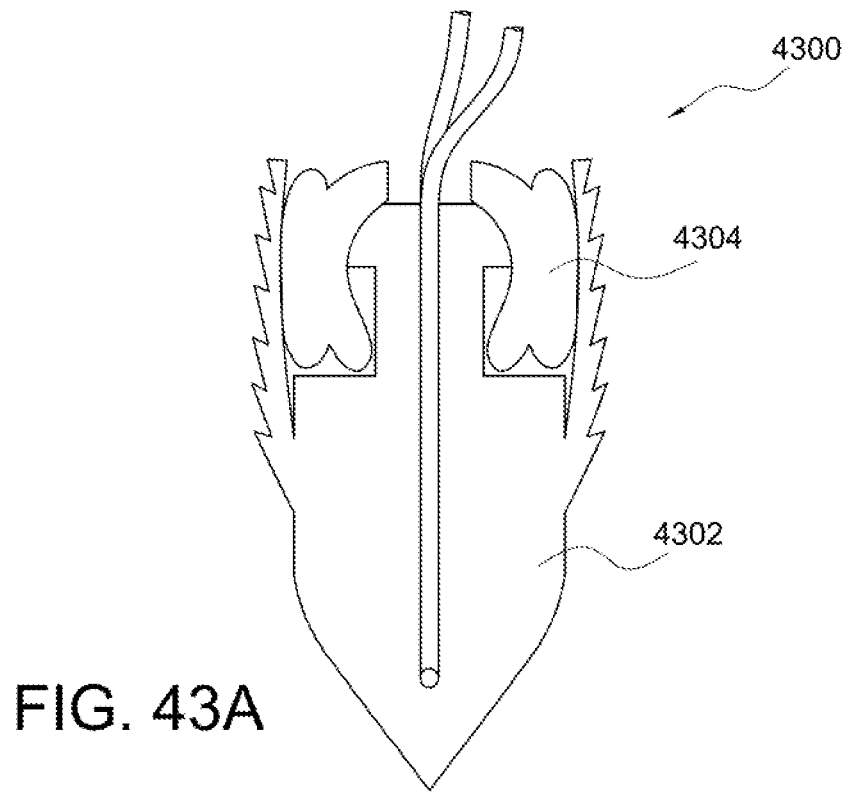
FIGS. 43A-43B illustrate still more features of an anchor prepared according to principles of the invention.
Figure 43B:
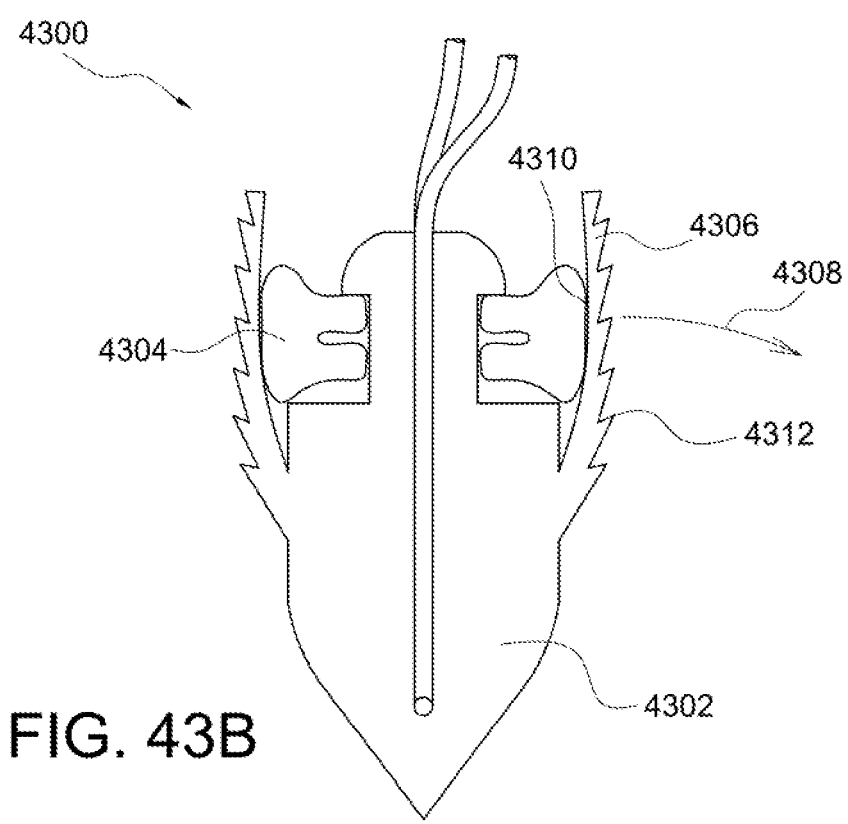

FIGS. 43A and 43B show, in sectional schematic view, a further arrangement of a suture anchor 4300 including a substantially rigid stopper portion 4302 and a flexible and/or elastic wadding portion 4304. The suture anchor 4300 is similar to anchor 4200 and includes the further feature of a flexible gripping portion 4306 arranged to be urged outwardly 4308 by a circumferential surface region 4310 of the flexible and/or elastic wadding portion 4304 as the elastic wadding portion transitions from an un-constricted to a constricted configuration. In certain embodiments, the flexible gripping portion 4306 will include a material that is substantially more rigid than the flexible and/or elastic wadding portion 4304. In certain embodiments, the flexible gripping portion will include a surface feature such as, for example, the plurality of barbs 4312 illustrated in the present figure. The surface features will be configured to improve a frictional interaction between the gripping portion 4306 and a surrounding surface of a receiving bone cavity. Again, one of skill in the art will appreciate that, in certain embodiments, a tool including a tamper portion will be beneficially employed in the installation of the suture anchor 4300.

While the exemplary embodiments described above have been chosen primarily from the field of soft tissue to bone reattachment, one of skill in the art will appreciate that the principles of the invention are equally well applied, and that the benefits of the present invention are equally well realized, in a wide variety of other applications, for example, the relative repositioning of multiple bone pieces and prosthetic devices. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. An anchor comprising:
a stopper portion and a fixing portion, said fixing portion having a surface disposed adjacent to a surface of said stopper portion so as to constrain a motion of said stopper portion within a tissue matrix, said fixing portion including a wadding feature, said wadding feature including a flexible portion, said flexible portion including a contiguous deployment suture with a first deployment suture portion and a second deployment suture portion, said flexible portion including a third sliding suture portion, said second deployment suture portion and said third sliding suture portion being disposed longitudinally within an axial cavity of said first deployment suture portion, said first deployment suture portion having a surface region adapted to be urged outwardly from a longitudinal axis of said stopper portion when tension is applied to said second deployment suture portion such that said wadding feature assumes a constricted configuration, whereby said wadding feature does not require contact with said surrounding tissue matrix to transition from an un-constricted configuration to said constricted configuration.

2. An anchor as defined in claim 1 wherein said deployment suture comprises a serpentine portion.

3. An anchor as defined in claim 1 wherein an inner surface region of said axial cavity includes a surface region that is substantially smooth at the scale of the suture diameter.

4. An anchor as defined in claim 1 wherein said surface of said stopper portion defines an acute angle with a circumferential surface of said stopper portion, such that said stopper portion tends to cock when said wadding feature transitions from said un-constricted configuration to said constricted configuration.

5. An anchor as defined in claim 4 wherein an edge of said surface of said stopper region is configured and adapted to become embedded into an adjacent region of said tissue matrix when said wadding feature transitions from said un-constricted configuration to said constricted configuration.

6. An anchor comprising:
a stopper portion and a fixing portion, said fixing portion having a surface disposed adjacent to a surface of said stopper portion so as to constrain a motion of said stopper portion within a tissue matrix, said fixing portion including a wadding feature, said wadding feature including a flexible portion, said flexible portion including a contiguous deployment suture with a first deployment suture portion and a second deployment suture portion, said flexible portion including a third sliding suture portion, said second deployment suture portion and said third sliding suture portion being disposed longitudinally within an axial cavity of said first deployment suture portion, said first deployment suture portion having a surface region adapted to be urged outwardly from a longitudinal axis of said stopper portion when tension is applied to said second deployment suture portion such that said wadding feature assumes a constricted configuration.

7. An anchor as defined in claim 6 wherein said wadding feature tends to rotate said further surface region of said stopper portion into contact with said surface matrix when said wadding feature is configured in said constricted configuration.

8. An anchor as defined in claim 6 wherein said wadding feature includes a suture material and wherein said constricted configuration includes a knotted configuration.

9. An anchor as defined in claim 6 wherein said stopper portion includes a generally cylindrical external surface region, said generally cylindrical external surface region including at least one detent feature.

10. An anchor as defined in claim 9 wherein said detent feature includes a transverse surface region disposed at an oblique angle with respect to a longitudinal axis of said generally cylindrical surface region.

11. An anchor as defined in claim 10 wherein said transverse surface region comprises an end surface region of said stopper portion.

12. An anchor as defined in claim 11 wherein said end surface region of said stopper portion comprises a proximal end surface region of said stopper portion.

13. An anchor as defined in claim 6 wherein said stopper portion further includes an internal surface region, said internal surface region defining a bore through said stopper portion, said bore having a portion of a suture disposed therewithin.

14. An anchor as defined in claim 13 wherein a longitudinal axis of said bore is disposed generally transverse to a longitudinal axis of said stopper.

* * * * *